US008523564B2

(12) United States Patent
Dellinger et al.

(10) Patent No.: US 8,523,564 B2
(45) Date of Patent: Sep. 3, 2013

(54) ORTHODONTIC TOOTH RETENTION SYSTEM

(76) Inventors: Eugene L. Dellinger, Fort Wayne, IN (US); Aron E. Dellinger, Leo, IN (US)

(*) Notice: Subject to any disclaimer, the term of this patent is extended or adjusted under 35 U.S.C. 154(b) by 0 days.

(21) Appl. No.: 13/032,069

(22) Filed: Feb. 22, 2011

(65) Prior Publication Data
US 2011/0143302 A1 Jun. 16, 2011

Related U.S. Application Data

(60) Division of application No. 12/488,050, filed on Jun. 19, 2009, now Pat. No. 8,147,244, which is a continuation-in-part of application No. 11/969,423, filed on Jan. 4, 2008, now Pat. No. 7,854,610, which is a continuation-in-part of application No. 11/689,674, filed on Mar. 22, 2007, now abandoned, which is a continuation-in-part of application No. 11/122,946, filed on May 5, 2005, now abandoned.

(51) Int. Cl.
*A61C 3/00* (2006.01)
(52) U.S. Cl.
USPC .................................. 433/18; 433/3; 433/24
(58) Field of Classification Search
USPC .......................................... 433/3, 18, 24, 163
See application file for complete search history.

(56) References Cited

U.S. PATENT DOCUMENTS

| 351,065 | A | 11/1886 | Miller |
|---|---|---|---|
| 532,722 | A | 1/1895 | Dennis |
| 3,353,271 | A | 11/1967 | Blechman |
| 3,890,714 | A | 6/1975 | Gores |
| 3,984,915 | A | 10/1976 | Noble et al. |
| 4,014,096 | A | 3/1977 | Dellinger |
| 4,015,333 | A | 4/1977 | Dellinger et al. |
| 4,017,973 | A | 4/1977 | Nelson |
| 4,183,141 | A | 1/1980 | Dellinger et al. |
| 4,243,386 | A | 1/1981 | Kawaguchi |
| 4,284,405 | A | 8/1981 | Dellinger |
| 4,311,463 | A | 1/1982 | Glattly |
| 4,360,341 | A | 11/1982 | Dellinger |
| 4,384,854 | A | 5/1983 | Garfinkel |

(Continued)

FOREIGN PATENT DOCUMENTS

| EP | 1658822 A2 | 5/2006 |
|---|---|---|
| EP | 1278477 B1 | 8/2006 |
| EP | 1723925 B1 | 9/2007 |
| WO | WO2008/115616 A1 | 9/2008 |

OTHER PUBLICATIONS

Sandler, P.J. et al., Magnets and Orthodontics, British Journal of Orthodontics, vol. 16 (1989), pp. 243-249. (Sandler).

(Continued)

*Primary Examiner* — Eric Rosen
(74) *Attorney, Agent, or Firm* — Faegre Baker Daniels LLP

(57) ABSTRACT

An orthodontic retainer system including retainer modules that are applied to adjacent teeth in a patient's mouth. The retainer modules may be provided in the form of mutually attracted members, such as magnets, that are temporary coupled on opposites sides of a delivery member for positioning and bonding to an adjacent pair of teeth. In one exemplary embodiment, the retainer modules have rounded and/or chamfered edges and sloped and curved lingual surfaces, and may include a magnet that is received and sealed within an enclosure or cover that has the same shape or profile as the magnet and is made of a wear-resistant biocompatible material.

24 Claims, 22 Drawing Sheets

(56) References Cited

U.S. PATENT DOCUMENTS

| | | | |
|---|---|---|---|
| 4,396,373 | A | 8/1983 | Dellinger |
| 4,424,030 | A | 1/1984 | Smiley et al. |
| 4,457,707 | A | 7/1984 | Smiley |
| 4,508,505 | A | 4/1985 | Smiley et al. |
| 4,511,330 | A | 4/1985 | Smiley et al. |
| 4,526,540 | A | 7/1985 | Dellinger |
| 4,551,096 | A | 11/1985 | Dellinger |
| 4,565,526 | A | 1/1986 | Kawata et al. |
| 4,595,361 | A * | 6/1986 | Blechman et al. ............ 433/18 |
| 4,609,350 | A | 9/1986 | Krause |
| 4,657,508 | A | 4/1987 | Dellinger |
| 4,671,767 | A | 6/1987 | Blechman et al. |
| 4,749,352 | A | 6/1988 | Nicholson |
| 4,813,869 | A | 3/1989 | Gatewood |
| 4,869,667 | A | 9/1989 | Vardimon |
| 4,871,310 | A | 10/1989 | Vardimon |
| 4,968,248 | A | 11/1990 | McColgan et al. |
| 5,002,077 | A | 3/1991 | Wiley |
| 5,205,736 | A | 4/1993 | Blechman |
| 5,305,768 | A | 4/1994 | Gross et al. |
| 5,334,015 | A | 8/1994 | Blechman |
| 5,362,769 | A | 11/1994 | Waller et al. |
| 5,630,715 | A * | 5/1997 | Voudouris ............ 433/8 |
| 5,678,998 | A | 10/1997 | Honkura et al. |
| 5,752,832 | A | 5/1998 | Vardimon et al. |
| 5,782,743 | A | 7/1998 | Russell |
| 5,788,493 | A | 8/1998 | Tanaka et al. |
| 5,954,506 | A | 9/1999 | Tanaka |
| 6,299,450 | B1 | 10/2001 | Honkura et al. |
| 6,382,965 | B1 | 5/2002 | Ruiz-Vela et al. |
| 6,390,812 | B1 | 5/2002 | Chishti et al. |
| 6,413,086 | B1 | 7/2002 | Womack |
| 6,485,298 | B2 | 11/2002 | Chishti et al. |
| 6,705,863 | B2 | 3/2004 | Phan et al. |
| 6,984,128 | B2 | 1/2006 | Breining et al. |
| 7,300,279 | B2 | 11/2007 | Amundsen |
| 2002/0137010 | A1 | 9/2002 | Honkura et al. |
| 2003/0124478 | A1 | 7/2003 | Amundsen |
| 2004/0054028 | A1 | 3/2004 | Hattori |
| 2004/0229191 | A1 | 11/2004 | Dietrich |
| 2004/0265767 | A1 * | 12/2004 | Devanathan ............ 433/9 |
| 2005/0100868 | A1 | 5/2005 | Karim et al. |
| 2005/0133058 | A1 | 6/2005 | Ding |
| 2005/0186526 | A1 | 8/2005 | Stewart et al. |
| 2006/0240373 | A1 | 10/2006 | Amundsen |
| 2006/0252001 | A1 | 11/2006 | Dellinger |
| 2007/0020583 | A1 | 1/2007 | Kojima |
| 2007/0065768 | A1 | 3/2007 | Nadav |
| 2007/0190476 | A1 | 8/2007 | Dellinger |
| 2008/0108007 | A1 | 5/2008 | Kong et al. |
| 2008/0176180 | A1 | 7/2008 | Dellinger |
| 2008/0199824 | A1 | 8/2008 | Hargadon |
| 2009/0305182 | A1 | 12/2009 | Dellinger |

OTHER PUBLICATIONS

Noar, J.H. et al., Rare Earth Magnets in Orthodontics: An Overview, British Journal of Orthodontics, vol. 26 (1999), pp. 29-37. (Noar).

Springate. S.D. et al., Micro-magnetic Retainers: An Attractive Solution to Fixed Retention, British Journal of Orthodontics, vol. 18 (1991), pp. 139-141. (Springate).

Donohue, V.E. et al., In Vitro Cytotoxicity Testing of Neodymium-Iron-Boron Magnets, Journal of Applied Biomaterials, vol. 6 (1995), pp. 69-74. (Donahue).

Darendeliler, A., Clinical application of magnets in orthodontics and biological implications: a review, European Journal of Orthodontics, vol. 19 (1997), pp. 431-442. (Darendililer).

Blechman, A.M., Pain-free and mobility-free orthodontics?, American Journal of Orthodontics and Dentofacial Orthopedics (1998), pp. 379-383. (Blechman).

The Office Action mailed Jun. 29, 2009 in related U.S. Appl. No. 11/969,423.

The Final Office Action mailed Jan. 13, 2010 in related U.S. Appl. No. 11/969,423.

European Search Report mailed Feb. 8, 2013 and the publication of the European Search Report as EP2263597A3 on Mar. 13, 2013.

* cited by examiner

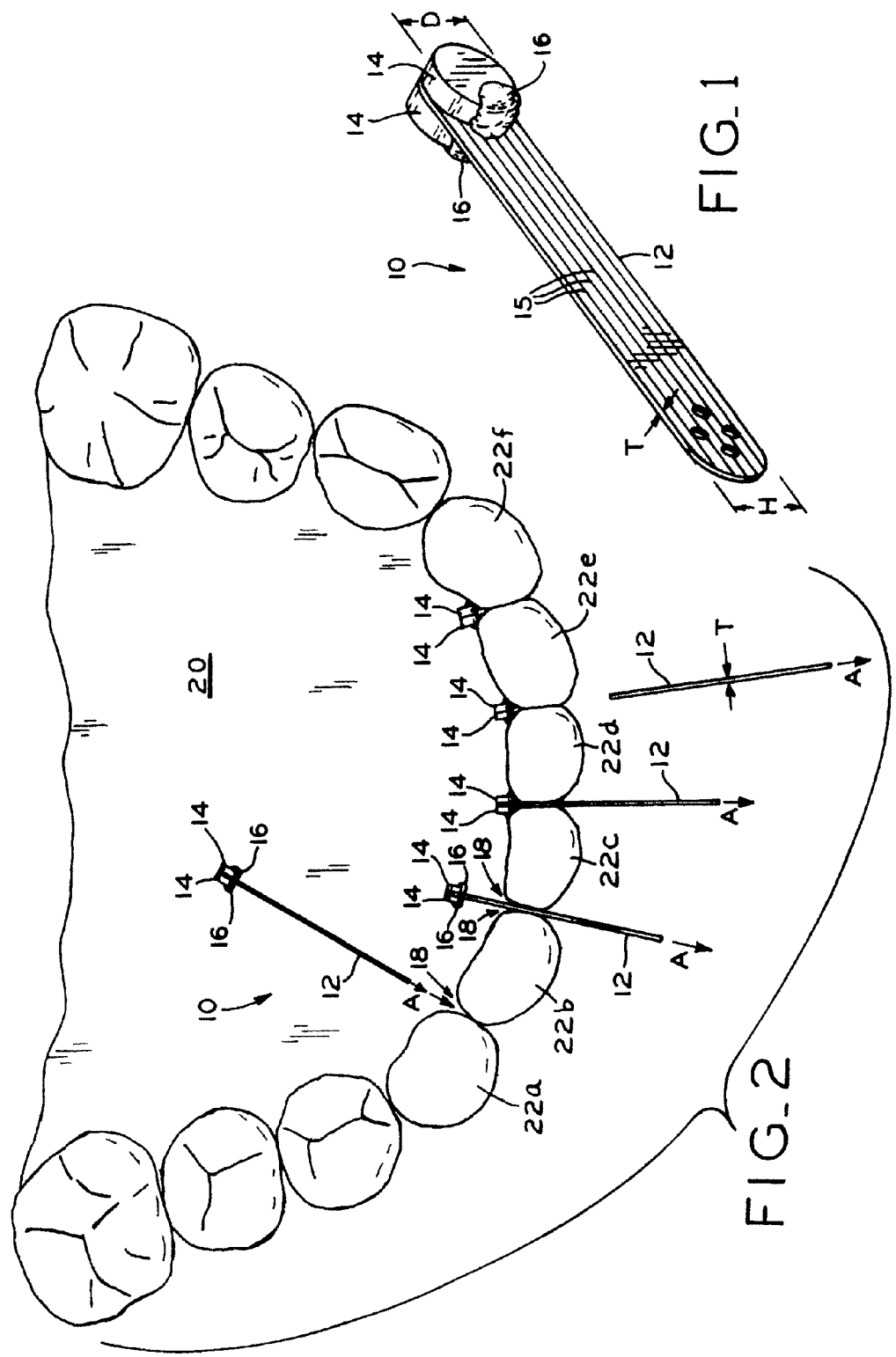
FIG_1
FIG_2

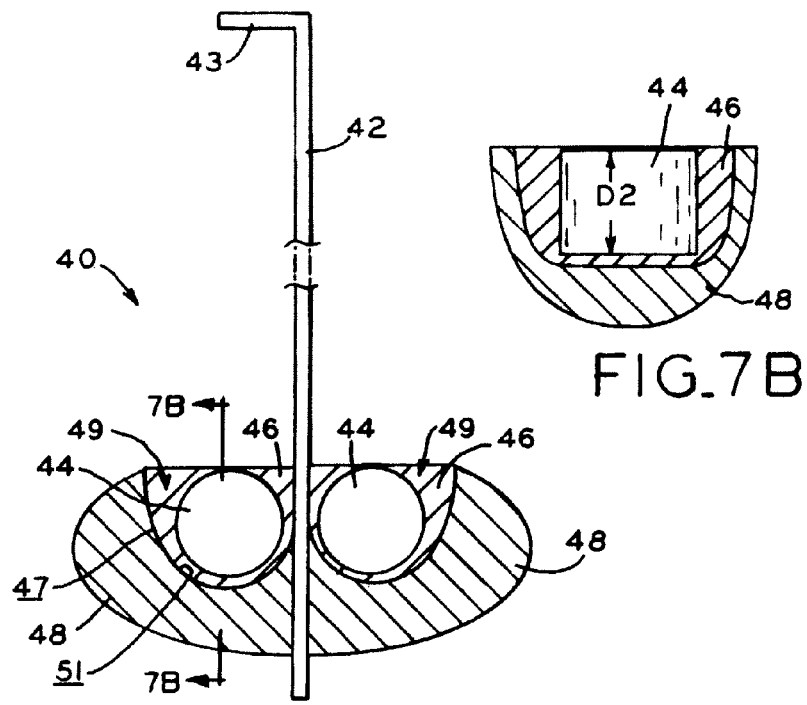
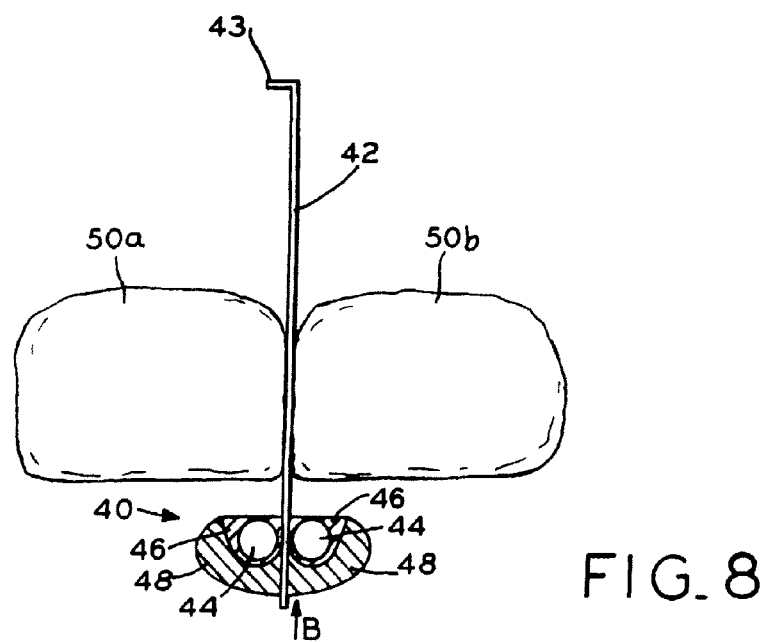

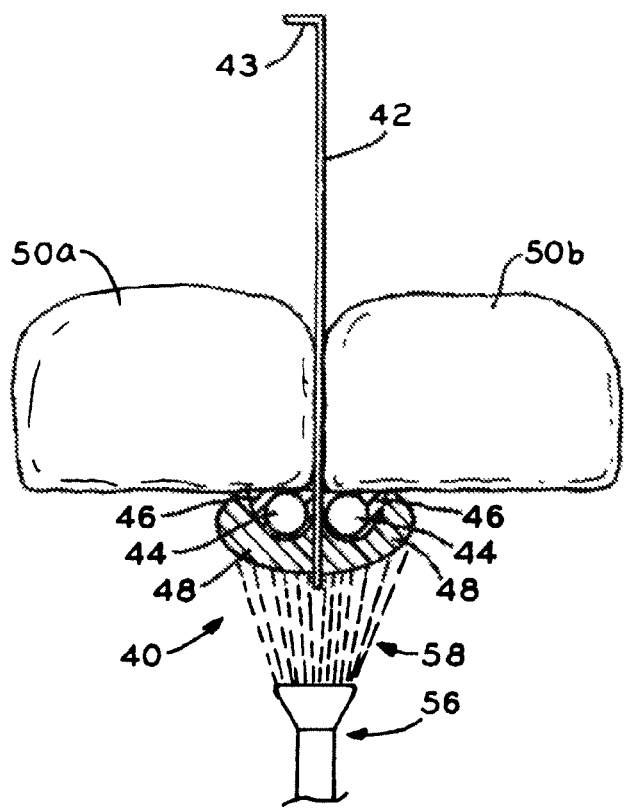
FIG._11
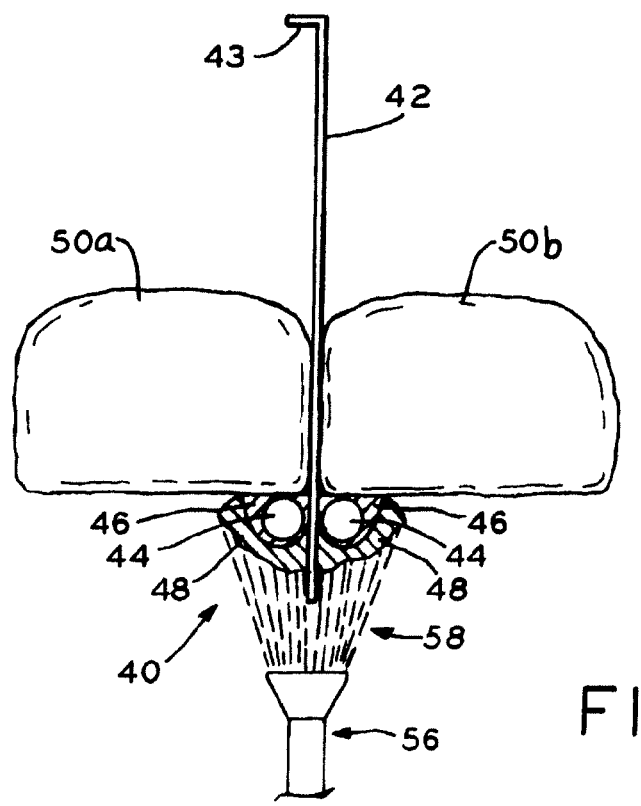
FIG._12

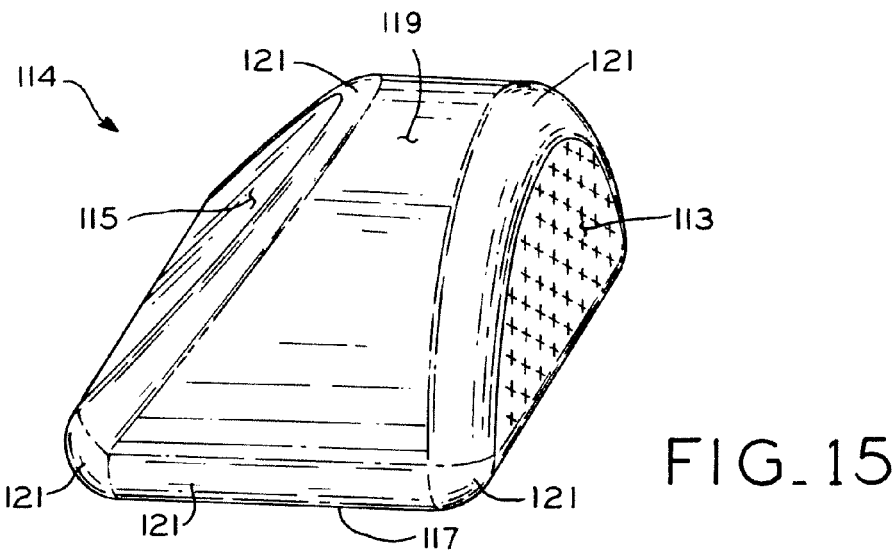
FIG_15
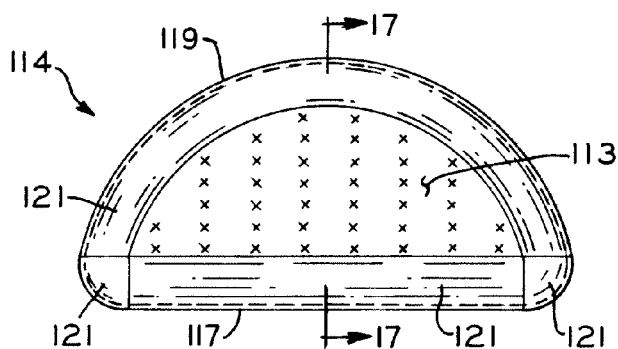
FIG_16
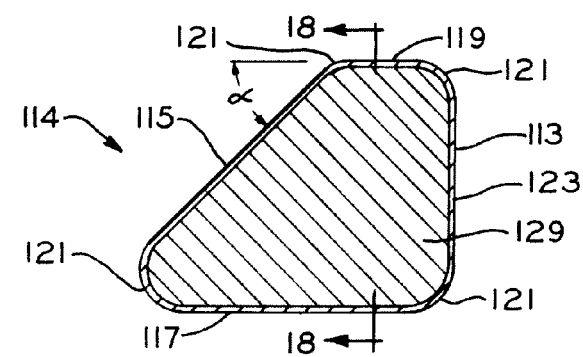
FIG_17
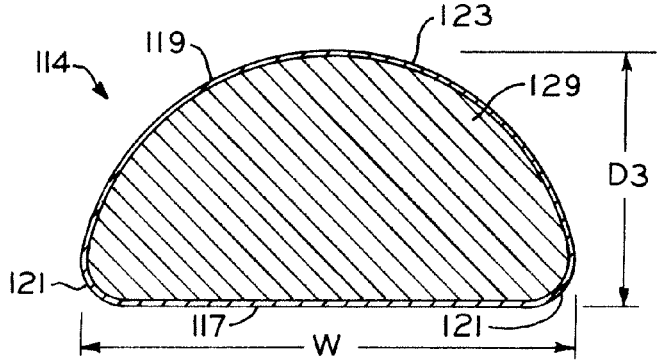
FIG_18

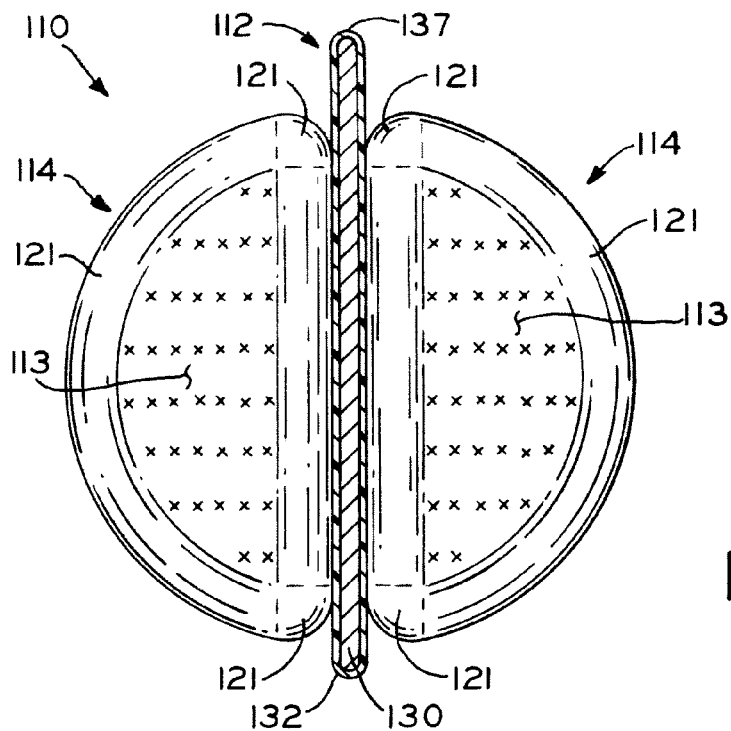
FIG_22
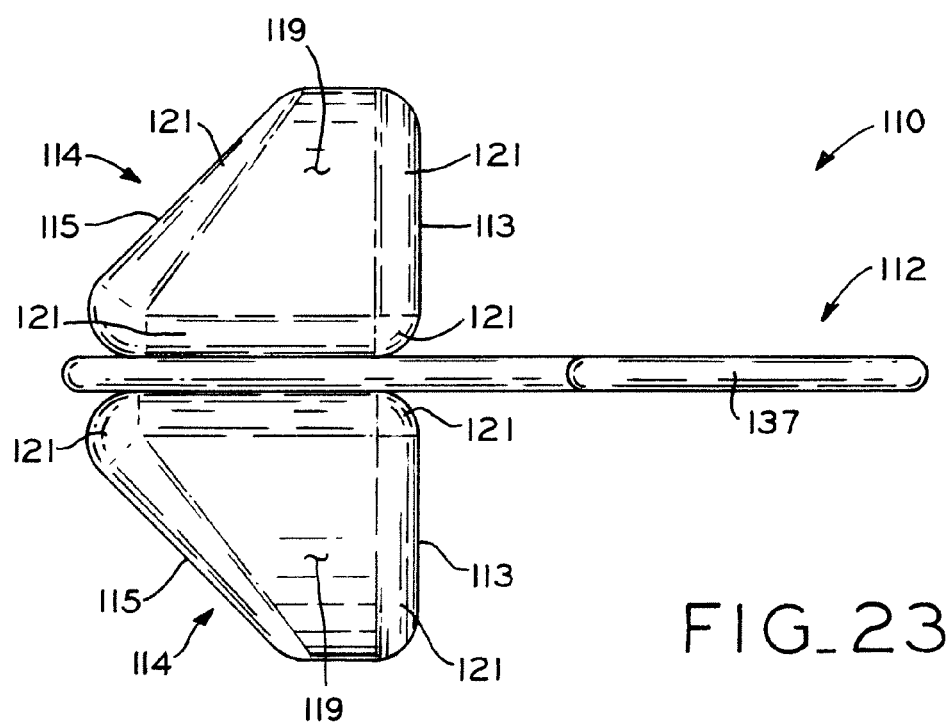
FIG_23

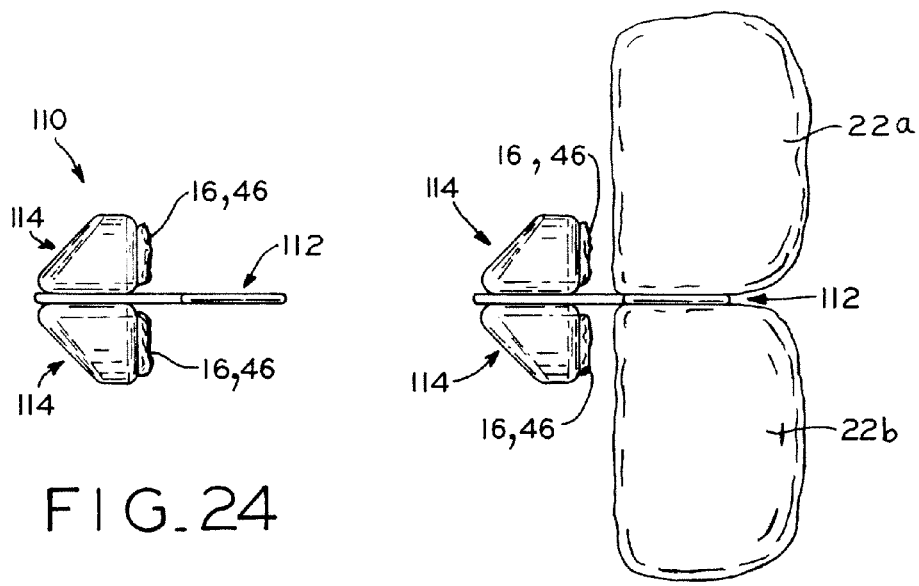
FIG.24
FIG.25
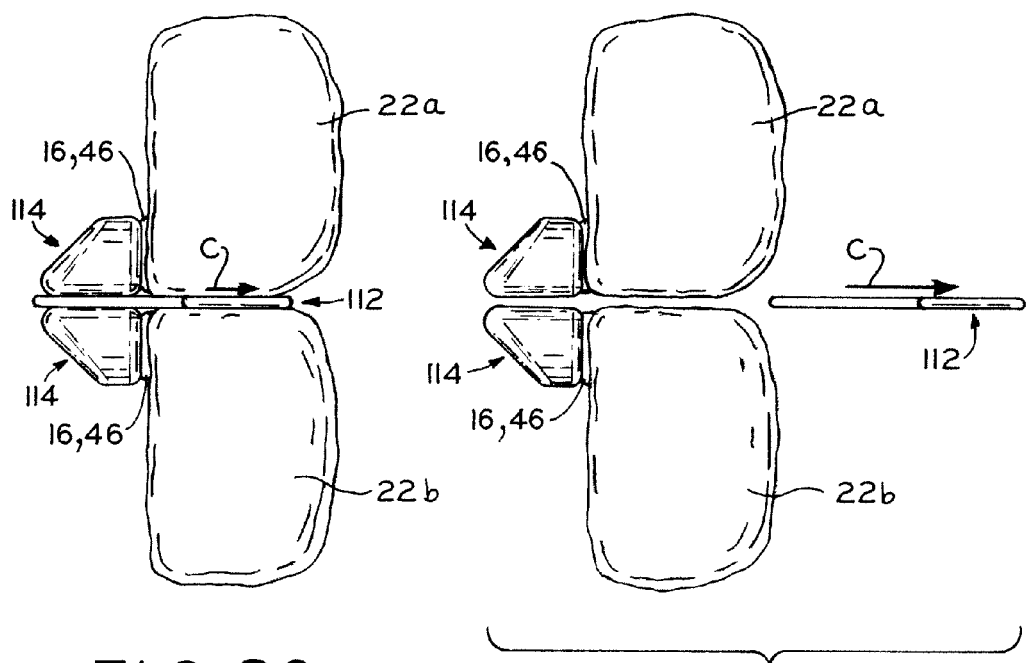
FIG.26
FIG.27

ORTHODONTIC TOOTH RETENTION SYSTEM

CROSS REFERENCE TO RELATED APPLICATIONS

This application is a divisional of U.S. application Ser. No. 12/488,050, entitled ORTHODONTIC TOOTH RETENTION SYSTEM, filed Jun. 19, 2009, and granted Apr. 3, 2012 as U.S. Pat. No. 8,147,244 which is a continuation-in-part of U.S. application Ser. No. 11/969,423, entitled ORTHODONTIC TOOTH RETENTION SYSTEM, filed on Jan. 4, 2008, and granted Dec. 21, 2010 as U.S. Pat. No. 7,854,610, which is a continuation-in-part of U.S. patent application Ser. No. 11/689,674, filed Mar. 22, 2007, entitled ORTHODONTIC TOOTH RETENTION SYSTEM, now abandoned, which is a continuation-in-part of U.S. patent application Ser. No. 11/122,946, filed May 5, 2005, entitled METHOD AND APPARATUS FOR POSITIONING AN ORTHODONTIC APPLIANCE, now abandoned, the entire disclosures of which are hereby expressly incorporated herein by reference.

BACKGROUND

1. Field of the Disclosure

The present disclosure relates to orthodontics, and, more particularly, to an orthodontic tooth retention system for delivering pairs of magnets for application to adjacent teeth to retain the teeth in a desired position.

2. Description of the Prior Art

Orthodontic appliances incorporating a variety of arrangements of mutually attracted elements, such as magnets, have been proposed. Some prior arrangements use magnets as a retaining device to retain teeth in a corrected position as a secondary function to primary tooth movement. Magnetic elements have also been used in combination with dentures for retaining the dentures in the mouth. When magnets are used as retaining devices, the magnets are placed onto teeth and the attractive force between the magnets provides a retaining force, thereby preventing the adjacent teeth from moving apart.

Other arrangements use magnets as corrective devices to move teeth into a corrected position. The conventional way for moving teeth in the mouth usually involves orthodontic appliances, such as braces and wires that exert a constant force on the tooth that needs to be moved. An elastic member creating the constant force must periodically be adjusted by a dentist or orthodontist. Many times dental appliances, including a retainer wire, are required across the front of the teeth to prevent excessive movement of the teeth.

SUMMARY

The present disclosure provides an orthodontic retainer system including retainer modules that are applied to adjacent teeth in a patient's mouth, and to a method and apparatus for delivering the system. The retainer modules may be provided in the form of mutually attracted members, such as magnets, that are temporary coupled on opposite sides of a delivery member for positioning and bonding to an adjacent pair of teeth. In one exemplary embodiment, the retainer modules have rounded and/or chamfered edges and a sloped lingual surface, and may include a magnet that is received and sealed within an enclosure or cover that has the same shape or profile as the magnet and is made of a wear-resistant biocompatible material. In one exemplary embodiment, the delivery member is substantially L-shaped, which advantageously allows an orthodontist to enter only a small portion of the patient's oral cavity to position the retainer modules on a patient's teeth, and eases the orthodontist's delivery of the retainer modules by substantially eliminating the need for the orthodontist to manipulate or otherwise move the patient's lips, tongue, and/or cheeks. The delivery member may also include pusher elements that contact the retainer modules for exerting a force against the modules to press same firmly against the teeth in order to enhance bonding between the modules and the teeth.

In another exemplary embodiment, the retainer system includes a magnet carrier portion having a recess which contains an adhesive material. The magnets may be embedded in the adhesive material. Once positioned on adjacent teeth, the adhesive material is cured and the carrier is removed to reveal an envelope or shaped profile of the adhesive material. The shaped profile of the adhesive material obviates the need to post-form adhesive material around the magnets after attaching the magnets to the adjacent teeth. Furthermore, the shaped profile may include a smooth surface. The adhesive material may also be aesthetically colored to match the coloring of the adjacent teeth. The carrier may be formed of a water soluble material or may be a flexible material.

In another embodiment, a method and apparatus for delivering an orthodontic appliance is provided wherein pairs of mutually attracted members, e.g., magnets, are applied to adjacent teeth, thereby retaining the teeth in a desired position, for example, after the teeth have been moved to new positions by conventional orthodontic techniques. The magnets may be very small magnets which may be gold plated. Generally, the magnets are biocompatible.

In an exemplary embodiment, the method of applying the magnets to the teeth includes placing two magnets on opposite sides of a thin metal strip, or a non-magnetic strip of material such as Mylar® material, available from DuPont Teijin Films, of Hopewell, Va. Because the magnets are attracted to each other, they will stay in place on opposite sides of the strip. An adhesive is applied to each magnet, and/or to the teeth to which the magnets will be secured. In one exemplary embodiment, primer material is applied to the adjacent teeth in the locations where the magnets are to be placed and the adhesive is applied to the magnets. The strip is then placed in the space between two adjacent teeth. The strip is then drawn forward between the adjacent teeth until the adhesive material on the magnets touches the primer material on the adjacent teeth. This allows ideal positioning of the magnets as determined by their individual magnetic fields. An ultraviolet or visible light source can be used to cure the adhesive, and retain each of the magnets in place on one of the two adjacent teeth. The strip is then removed by pulling it through the space between the adjacent teeth, thereby leaving behind the magnets secured to the adjacent teeth. The magnets will retain the adjacent teeth in their positions because of the magnetic attraction between the magnets.

In one form thereof, the present invention provides an orthodontic retainer system for use on teeth, including: a delivery member, including: a gripping portion extending along a gripping portion axis; and a retention portion extending along a retention portion axis, the gripping portion joined to the retention portion at an angle such that the delivery member is substantially L-shaped; and a pair of dental modules coupled to the delivery member.

In another form thereof, the present invention provides a dental module for use on teeth as part of an orthodontic retainer system, including: a tooth engaging surface; a bottom surface having opposing ends, wherein a distance between the opposing ends of the bottom surface defines a width of the dental module, the bottom surface forming a first angle with the tooth engaging surface; a lingual surface forming a second angle with at least one of the tooth engaging surface and the bottom surface, wherein the second angle is less then ninty degrees; and at least one chamfered edge defined between at least one of the tooth engaging surface, the bottom surface, and the lingual surface and another of the tooth engaging surface, the bottom surface, and the lingual surface.

In yet another form thereof, the present invention provides a method of applying a dental module to a tooth having a lingual side, including the steps of: providing a substantially L-shaped delivery member; positioning at least one dental module on the delivery member; inserting the delivery member between a pair of adjacent teeth; advancing the delivery member in an anterior direction to remove the delivery member from between the pair of adjacent teeth.

In a further form thereof, the present invention provides an orthodontic retainer system for use on teeth, including a pair of retainer modules, each including a cover member made of a first, biocompatible material and including an interproximal surface; a magnet received within the cover member; and a tooth-facing bonding surface; and a delivery member including a strip of material disposed between the retainer modules, the interproximal surfaces of the cover members in direct engagement with respective opposite sides of the strip with the retainer modules coupled to the strip by mutual magnetic attraction of the magnets.

In a further form thereof, the present invention provides a method of applying a pair of retainer modules respectively to a pair of adjacent teeth for use in aiding the retention of relative positions of the teeth, the method including the steps of: placing a pair of magnetic retainer modules on respective opposite sides a delivery member in the form of a strip of material, with interproximal surfaces of the retainer modules directly engaging the strip and the strip captured between the retainer modules by mutual magnetic attraction of the retainer modules; inserting the strip between a pair of adjacent teeth along a direction from occlusal surfaces of the teeth toward the gum tissue between the teeth to position the retainer modules adjacent respective lingual sides of the adjacent teeth; moving the strip along a lingual-facial direction to move the retainer modules toward the lingual sides of the adjacent teeth; capturing the retainer modules between a pair of pusher elements fixed to the strip and the lingual sides of the adjacent teeth; securing the retainer modules to the lingual sides of the adjacent teeth with an adhesive; and withdrawing the strip from between the adjacent teeth along a direction from the gum tissue between the teeth toward the occlusal surfaces of the teeth.

BRIEF DESCRIPTION OF THE DRAWINGS

The above mentioned and other features of this disclosure, and the manner of attaining them, will become more apparent and will be better understood by reference to the following description of embodiments of the disclosure taken in conjunction with the accompanying drawings, wherein:

FIG. 1 is a perspective view of a delivery member of the present disclosure, further illustrating a coupled pair of mutually attracted members;

FIG. 2 is an occlusal view of an individual's teeth, further illustrating the several steps of the method of the present disclosure;

FIG. 7A is a partial sectional occlusal view of an orthodontic retainer system according to another embodiment of the present disclosure;

FIG. 7B is a cross-sectional view of a portion of the system of FIG. 7A, taken along line 7B-7B of FIG. 7A;

FIGS. 8-14 are partial sectional occlusal views of exemplary steps in a method of attaching a pair of magnets to a pair of adjacent teeth, wherein:

FIG. 8 shows the pair of magnets spaced from the pair of adjacent teeth before attachment thereto;

FIG. 9 shows the pair of magnets temporarily attached to the pair of adjacent teeth prior to curing the adhesive material;

FIG. 10 shows a curing instrument for curing the adhesive material;

FIG. 11 shows an instrument for dispensing water onto the system;

FIG. 12 shows the carrier partially dissolved;

FIG. 13 shows the carrier completely dissolved to reveal the adhesive material profile;

FIG. 14 shows the removal of an alternative carrier with a dental instrument;

FIG. 15 is a perspective view of a mutually attractive member according to another exemplary embodiment;

FIG. 16 is a lingual view of the mutually attractive member of FIG. 15;

FIG. 17 is a cross-sectional view of the mutually attractive member of FIG. 16 taken along line 17-17 of FIG. 16;

FIG. 18 is a cross-sectional view of the mutually attractive member of FIG. 17 taken along line 18-18 of FIG. 17;

FIG. 22 is a cross-sectional view of the delivery member of FIG. 21, further illustrating the pair of coupled mutually attractive members of FIG. 21;

FIG. 23 is an occlusal view of the delivery member and pair of coupled mutually attractive members of FIG. 21;

FIG. 24 is an occlusal view of the delivery member and mutually attractive members of FIG. 23, further illustrating adhesive positioned on the mutually attractive members;

FIGS. 25-27 are partial sectional occlusal views of exemplary steps in a method of attaching the pair of mutually attractive members to a pair of adjacent teeth, wherein;

FIG. 25 shows the pair of mutually attractive members spaced from the pair of adjacent teeth before attachment thereto;

FIG. 26 shows the pair of mutually attractive members attached to the pair of adjacent teeth;

FIG. 27 shows the delivery member separated from the pair of mutually attractive members;

Figure 3:
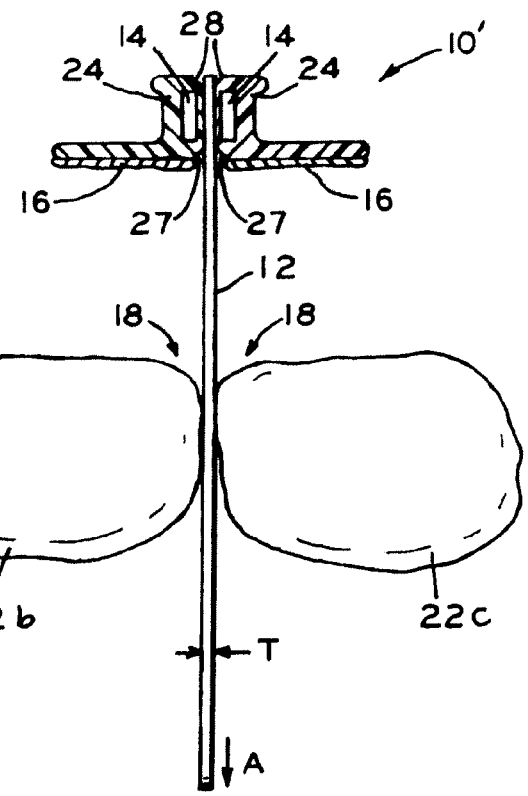
FIG. 3 is an occlusal view of a portion of an individual's teeth, further illustrating an alternative embodiment orthodontic retainer system according to the present disclosure.

Corresponding reference characters indicate corresponding parts throughout the several views. Although the exemplifications set out herein illustrate the disclosure, the embodiments disclosed below are not intended to be exhaustive or to be construed as limiting the scope of the invention to the precise forms disclosed.

DETAILED DESCRIPTION

The present disclosure provides an orthodontic retainer system including retainer modules that are applied to adjacent teeth in a patient's mouth, and to a method and apparatus for delivering the system. The retainer modules may be provided in the form of mutually attracted members, such as magnets, that are temporary retained on a delivery member for positioning and bonding to an adjacent pair of teeth. In one exemplary embodiment, the retainer modules have rounded and/or chamfered edges and sloped and curved lingual surfaces, and may include a magnet that is received and sealed within an enclosure or cover that has the same shape or profile as the magnet and is made of a wear-resistant biocompatible material. In one exemplary embodiment, the delivery member is substantially L-shaped, which advantageously allows an orthodontist to enter only a small portion of the patient's oral cavity to position the retainer modules on a patient's teeth, and eases the orthodontist's delivery of the retainer modules by substantially eliminating the need for the orthodontist to manipulate or otherwise move the patient's lips, tongue, and/or cheeks. The delivery member may also include pusher elements that contact the retainer modules for exerting a force against the modules to press same firmly against the teeth in order to enhance bonding between the modules and the teeth.

Referring now to FIG. 1, orthodontic retainer system 10 is shown, including strip or delivery member 12 and mutually attracted dental modules 14. Mutually attracted dental modules 14 are releasably coupled by attractive forces to opposite sides of delivery member 12. The phrase "mutually attracted dental modules," for the purposes of this document, generally means two separate bodies which have a mutual attraction for each other and which are suitable for placement in the mouth for a period of time. For example, in one embodiment, each mutually attracted dental module 14 may comprise a magnet or any other suitable device capable of mutual attraction, i.e., electrostatic members. When mutually attracted dental modules 14 are magnets, they are coupled together on opposite sides of delivery member 12 via magnetic forces, with delivery member 12 captured between modules 14. Each mutually attracted dental module 14 has a dimension D (FIG. 1), such as a height or a diameter, in the range of 0.010 to 0.040 inches (0.254 mm to 1.016 mm), preferably in the range of 0.038 to 0.039 inches (0.9652 mm to 0.991 mm). In one form thereof, mutually attracted dental module 14 is in the shape of a cylinder, as shown in FIG. 1. Mutually attracted dental module 14 may also take different forms, including those having cross-sectional shapes such as various polygonal shapes. Each mutually attracted dental module 14 is made of a biocompatible material to allow its implantation in the mouth for a period of time. For example, each mutually attracted dental module 14 may be gold-plated, or, alternatively, could be comprised entirely of gold. In another embodiment, each mutually attracted dental module 14 comprises neodymium iron. As shown in FIG. 1, a quantity of adhesive 16 can be applied to an anterior face of each mutually attracted dental module 14 to facilitate securement of the same to a tooth.

Referring to FIGS. 1 and 2, delivery member 12 is a thin, non-magnetic strip of material, such as Mylar™ material, having a thickness T which, in one embodiment, may be may be as small as 0.001, 0.002, 0.003, 0.004, or 0.005 inches (0.0254 mm, 0.0508 mm, 0.0762 mm, 0.1016 mm, or 0.127 mm) or as large as approximately 0.012, 0.011, 0.010, 0.009, 0.008, 0.007, or 0.006 inches (0.3048 mm, 0.2794 mm, 0.254 mm, 0.2286 mm, 0.2032 mm, 0.1778 mm, or 0.1524 mm). Thickness T is such as to allow delivery member 12 to pass between a pair of adjacent teeth 22, for example, teeth 22a and 22b. The length of delivery member 12 can be any size to facilitate an easy access for an orthodontist for pulling delivery member 12 between a pair of adjacent teeth 22a and 22b, as will be described hereinbelow. Delivery member 12 may also include scribe marks 15 which may be lettered or numbered accordingly to provide a depth gauge, thereby providing the orthodontist with an indication of the depth of delivery member 12 with respect to adjacent teeth 22. In an alternative embodiment, delivery member 12 may be part of a continuous piece of material which has pairs of mutually attracted dental modules 14 carried thereon at various spaced distances. The orthodontist would then cut the continuous piece of material just beyond the location of mutually attracted dental modules 14 to obtain a single orthodontic retainer system 10. Height H of delivery member 12 may range from 0 to 10 millimeters, but height H may be increased depending on the desired application.

Referring now to FIG. 2, the method of applying magnetic orthodontic retainer system 10 will be described. Mouth 20 is shown including a plurality of teeth 22a-22f. In one embodiment, a pair of mutually attracted dental modules 14 are placed on opposite sides of delivery member 12, whereby the attractive coupling between mutually attracted dental modules 14 retains them in place on delivery member 12. Mutually attracted dental modules 14 are not bonded to delivery member 12, rather, delivery member 12 functions to carry mutually attracted dental modules 14 to their final destination on adjacent teeth. A quantity of adhesive 16 is then placed on mutually attracted dental modules 14, or, alternatively, adhesive 16 may be applied to mutually attracted dental modules 14 prior to placing modules 14 on opposite sides of delivery member 12. Furthermore, primer material 18 is applied to a posterior surface of adjacent teeth 22, i.e., teeth 22b and 22c, in a location where adhesive 16 applied to mutually attracted dental modules 14 will contact the surface of teeth 22b and 22c. Primer material 18 may comprise a material such as acid for etching a posterior surface of each tooth 22. Primer material 18 may also comprise chemical etching or any type of material to facilitate bonding with adhesive 16.

Referring still to FIG. 2, delivery member 12, with mutually attracted dental modules 14 carried thereon, is placed between a pair of adjacent teeth, for example, between teeth 22b and 22c. Delivery member 12 is then pulled in the general direction of Arrow A, as shown by delivery member 12 being pulled between teeth 22b and 22c. Arrow A generally indicates an anterior direction, i.e., towards the front of the mouth or from the lingual side of the teeth towards the facial side of the teeth. Delivery member 12 is pulled until the pair of mutually attracted dental modules 14 contacts the teeth, as shown, for example, by mutually attracted dental modules 14 contacting teeth 22c and 22d. At this point, adhesive 16 contacts primer material 18. Adhesive 16 is then cured to harden adhesive 16 and attach mutually attracted dental modules 14 to teeth 22c and 22d. In one embodiment, an ultraviolet or visible light source (not shown) may be used to cure adhesive 16.

To complete the operation, delivery member 12 is pulled further anteriorly to remove delivery member 12 from between any teeth, for example, as shown by delivery member 12 removed from between teeth 22d and 22e. Once delivery member 12 has been completely removed, mutually attracted dental modules 14 remain attached to teeth 22e and 22f, for example, to provide an orthodontic retainer system. Because mutually attracted dental modules 14 are not secured to delivery member 12 and are only carried thereon via the mutual attraction between mutually attracted dental modules 14, delivery member 12 simply slides between mutually attracted dental modules 14 and the adjacent teeth to which modules 14 are attached for removal of delivery member 12 from mouth 20. Movement of delivery member 12 after curing will not disturb dental modules 14 because the force coupling dental modules 14 to delivery member 12 is less than the force adhering dental modules 14 to the teeth. Once placed, mutually attracted dental modules 14 retain adjacent teeth without the need for other, more cumbersome orthodontic appliances. In most cases, depending on the spacing between the adjacent teeth, the mutually-facing surfaces of modules 14 will contact each other via magnetic attraction to aid in retaining the teeth in position.

Although the above-described embodiments describe mutually attracted dental modules 14, the present disclosure also contemplates a method and apparatus for positioning mutually repelled dental modules (not shown). In this embodiment, mutually repelled dental modules could be positioned on adjacent teeth such that the mutually repelled dental modules repel one another to move the adjacent teeth to a corrected position. The mutually repelled dental modules could be detachably adhered to delivery member 12 with a force less than the force adhering the mutually repelled dental modules to the teeth. In one embodiment, the mutually repelled dental modules may be magnets. If the mutually repelled dental modules comprise magnets, the magnets would be oriented in a repelling, non-attractive position, for example, with the north pole of one mutually repelled dental module lined up with the north pole of the other mutually repelled dental module. In contrast and as described above, mutually attracted dental modules 14 would be positioned such that, if modules 14 were magnets, the south pole of one module 14 would line up with the north pole of another module 14, such as to provide an attractive force between the two modules 14. Mutually repelled dental modules could be delivered and positioned on adjacent teeth in the mouth in a substantially identical manner as described above for modules 14.

Figure 4:
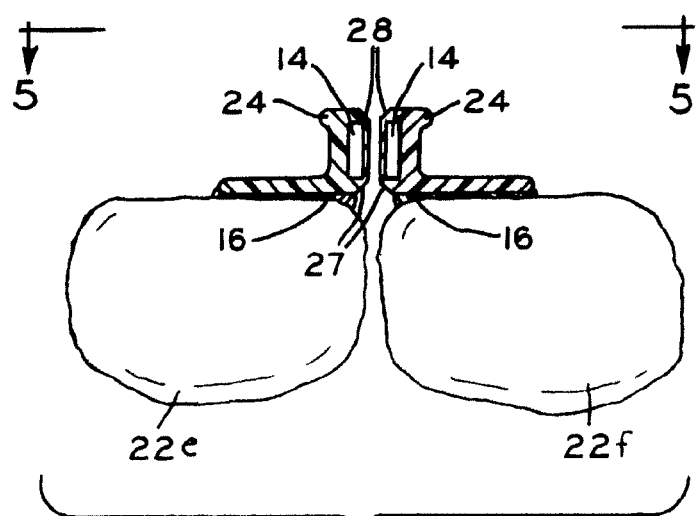
FIG. 4 is an occlusal view of a portion of an individual's teeth, further illustrating the orthodontic retainer system of FIG. 3.
Figure 5:
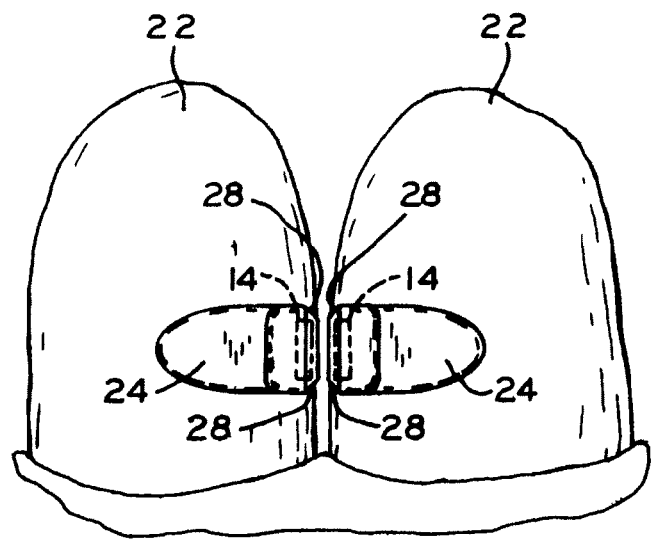
FIG. 5 is a posterior view of the portion of an individual's teeth shown in FIG. 4.
Figure 6:
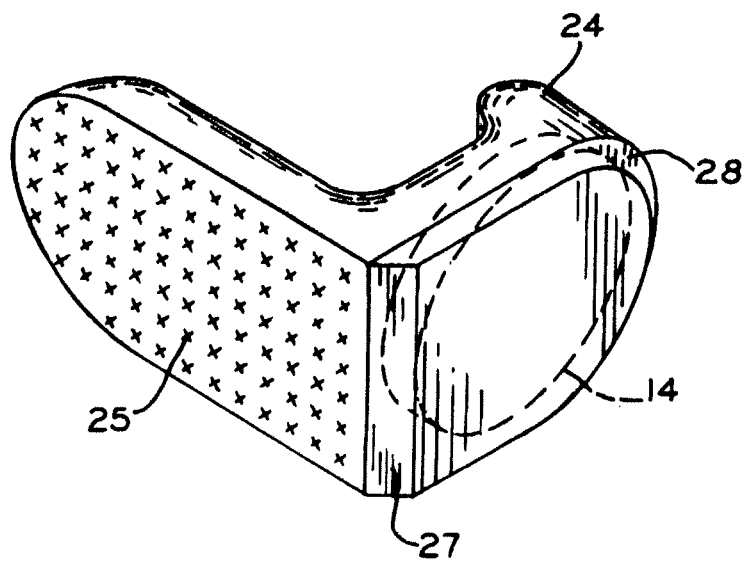
FIG. 6 is a perspective view of a capsule of the present disclosure, further illustrating a mutually attracted dental module encapsulated therein.

Referring now to FIG. 3, in an alternative embodiment, orthodontic retainer system 10' is shown, including strip or delivery member 12 and mutually attracted dental modules 14 encapsulated within capsules 24. Capsules 24 may be formed of metal, ceramic, composite, or any other suitable biocompatible material. In an exemplary embodiment, capsule 24 should not include any sharp edges or irritating features such as features which possibly could cause harm to the tongue or other portions of the mouth. Referring now to FIG. 6, capsule 24 may include surface 25 which facilitates the application of adhesive 16 to capsule 24. Surface 25 may be a grid, mesh, or series of geometric undercuts in capsule 24 to provide an abrasive surface to which adhesive 16 is applied. Capsule 24 may include beveled edge 27 and beveled edge 28. Beveled edges 27 and 28 are provided to facilitate flossing of adjacent teeth 22 after capsules 24 are delivered. Beveled edges 27 and 28 are oriented such that a V-shaped groove is provided on both an upper portion and a lower portion of adjacent capsules 24, as shown in FIG. 5. Beveled edges 27 and 28 are also designed such that a V-shaped groove is provided on both an anterior portion and a posterior portion of adjacent capsules 24, as shown in FIG. 4.

Referring again to FIG. 3, mutually attracted dental modules 14 are used in a substantially identical way as described above wherein mutually attracted dental modules 14 are releasably coupled by attractive forces to opposite sides of delivery member 12.

The method of applying magnetic orthodontic retainer system 10' is substantially identical to the method described above for applying magnetic orthodontic retainer system 10. Referring now to FIGS. 3 and 4, the mutual attraction of mutually attracted dental modules 14 retain both capsule 24 and module 14 in place on delivery member 12. Capsules 24 are not bonded to delivery member 12, rather, capsules 24 are held in place via the mutual attraction of mutually attracted dental modules 14 contained therein. A quantity of adhesive 16 is then placed on capsule 24 on surface 25, or, alternatively, adhesive 16 may be applied to capsule 24 prior to placing capsules 24 and modules 14 on opposite sides of delivery member 12. Furthermore, primer material 18 is applied to a posterior surface of adjacent teeth 22, i.e., teeth 22b and 22c, in a location where adhesive 16 applied to capsules 24 will contact the surface of teeth 22b and 22c. Primer material 18 may comprise a material such as acid for etching a posterior surface of each tooth 22. Primer material 18 may also comprise chemical etching or any type of material to facilitate bonding with adhesive 16.

Similar to the method described above, delivery member 12, with mutually attracted dental modules 14 and capsules 24 carried thereon, is placed between a pair of adjacent teeth, for example, between teeth 22b and 22c. Delivery member 12 is then pulled in the general direction of Arrow A, as shown by delivery member 12 being pulled between teeth 22b and 22c. Delivery member 12 is pulled until the pair of capsules 24 contacts adjacent teeth. At this point, adhesive 16 contacts primer material 18. Adhesive 16 is then cured to harden adhesive 16 and attach capsules 24 to teeth 22. In one embodiment, an ultraviolet or visible light source (not shown) may be used to cure adhesive 16.

To complete the operation, delivery member 12 is pulled further anteriorly to remove delivery member 12 from between any teeth, for example, as shown by delivery member 12 removed from between teeth 22e and 22f. Once delivery member 12 has been completely removed, capsules 24, with mutually attracted dental modules 14 retained therein, remain attached to teeth 22e and 22f, for example, to provide an orthodontic retainer. Because capsules 24 are not secured to delivery member 12 and are only carried thereon via the mutual attraction between mutually attracted dental modules 14, delivery member 12 simply slides between capsules 24 and the adjacent teeth to which capsules 24 are attached for removal of delivery member 12 from mouth 20. Movement of delivery member 12 after curing will not disturb capsules 24 because the force coupling capsules 24 to delivery member 12 is less than the force adhering capsules 24 to the teeth. Once placed, mutually attracted dental modules 14 within capsules 24 retain adjacent teeth without the need for other, more cumbersome orthodontic appliances.

Orthodontic retainer system (not shown) may include capsules made of mutually attractive material. In one embodiment, the capsules may be formed as a single entity with no separate mutually attracted dental module contained therein. The capsules could be formed through an injection molding process wherein the entire capsule would be formed into a mutually attracted dental body, for example, a magnet. In one embodiment, the capsule may be entirely formed of magnetic material.

Although orthodontic retainer systems 10 and 10' have only been shown as being applied to adjacent anterior teeth in the lower portion of the mouth, the systems may also be applied to any adjacent teeth located anywhere in the mouth. Furthermore, in an alternative embodiment (not shown), orthodontic retainer systems 10 and 10' may be applied in any position on adjacent teeth as opposed to a lingual position as described hereinabove.

The method of application for orthodontic retainer systems 10 and 10' described above may also be used in an alternative, indirect application. In an alternative embodiment, orthodontic retainer system 10 or 10' is applied to an identical, non-human version of mouth 20, for example, a formed mold of mouth 20 including teeth 22. Orthodontic retainer system 10 or 10' is applied to the formed mold of teeth 22 in an identical fashion as described above. After application to the mold, an orthodontist could use any indirect technique commonly known by the dental profession to simultaneously remove all capsules 24 and/or modules 14 and simultaneously apply all capsules 24 and/or modules 14 in the corresponding patient's mouth 20. All capsules 24 and/or modules 14 may be included in a delivery tray or elastic material having the capability to simultaneously move all capsules 24 and/or modules 14 from the mold to mouth 20.

Referring now to FIGS. 7A and 7B, orthodontic retainer system 40 according to another embodiment is shown and may generally include delivery member 42 with handle 43, magnets 44, adhesive 46, and carrier 48. Magnets 44 are releasably coupled by their attractive magnetic forces to opposite sides of delivery member 42. Each magnet 44 may have a first dimension (FIG. 7A), such as a diameter, which may be as small as approximately 0.025, 0.030, 0.035, 0.040, or 0.045 inches (0.635 mm, 0.762 mm, 0.889 mm, 1.016 mm, or 1.143 mm) or as large as approximately 0.065, 0.060, 0.055, or 0.050 inches (1.651 mm, 1.524 mm, 1.397 mm, or 1.27 mm), for example. In one form thereof, magnet 44 may be in the shape of a cylinder. Magnet 44 may have a second dimension D2 (FIG. 7B), which may be as small as approximately 0.025, 0.030, 0.035, 0.040, or 0.045 inches (0.635 mm, 0.762 mm, 0.889 mm, 1.016 mm, or 1.143 mm) or as large as approximately 0.065, 0.060, 0.055, or 0.050 inches (1.651 mm, 1.524 mm, 1.397 mm, or 1.27 mm), for example. Magnet 44 may also take different shapes or forms, including cross-sectional shapes such as various polygonal shapes. Each magnet 44 may be formed of a biocompatible material to allow its implantation in the mouth for a period of time. For example, each magnet 44 may be formed either partially or completely of gold or neodymium iron and, in one embodiment is a neodymium iron magnet having a gold coating.

Delivery member 42 may be substantially similar to delivery members 12, 112 described above, except as described below. For example, delivery member 42 may be a thin, non-magnetic strip of material, such as Mylar® material, having a thickness T which, in one embodiment, may be as small as 0.001, 0.002, 0.003, 0.004, or 0.005 inches (0.0254 mm, 0.0508 mm, 0.0762 mm, 0.1016 mm, or 0.127 mm) or as large as approximately 0.012, 0.011, 0.010, 0.009, 0.008, 0.007, or 0.006 inches (0.3048 mm, 0.2794 mm, 0.254 mm, 0.2286 mm, 0.2032 mm, 0.1778 mm, or 0.1524 mm), for example. Thickness T is such as to allow delivery member 42 to pass between a pair of adjacent teeth 50a, 50b. Delivery member 42 may also be formed of a flexible plastic material, such as Mylar® material, for example, or, alternatively, a metal material, such as stainless steel, for example. In one embodiment, delivery member 42 includes a release coating, for example, a silicone, polyethylene, or fluoropolymer coating, such as polytetrafluoroethylene (PTFE) which is commercially available as Teflon® from E. I. du Pont de Nemours and Company of Wilmington, Del.; Silicon Premium, a siloxane release coating commercially available from General Electric Company of Waterford, N.Y.; and Clearsil® fluorosilicone release films and ClearLES™ silicone release liners commercially available from CPFilms, Inc. of Martinsville, Va. The length of delivery member 42 can be any size to facilitate an easy access for an orthodontist for pulling delivery member 42 between a pair of adjacent teeth 50a, 50b. Delivery member 42 may include handle 43 to facilitate movement of delivery member 42.

Adhesive 46 may be substantially similar to adhesive 16, described above with reference to FIGS. 1-4, except as described below. Magnets 44 may be at least partially encapsulated within, or enveloped by, adhesive 46. Adhesive 46 may be any adhesive suitable for a dental application, such as OptiBond®, available from Kerr Corporation of Orange, Calif.; Adper™ and Scotchbond™ adhesives available from 3M Corporation of St. Paul, Minn.; or Xeno® Light Cured Dental Adhesive available from DENTSPLY of York, Pa.

Carrier 48 may include recess 49 defining inner surface 51. Inner surface 51 conforms around magnet 44 and adhesive 46 and, after carrier 48 is removed in the manner described below, defines surface 47 of adhesive 46, which is an envelope or profile of adhesive surrounding magnets 44. Adhesive 46 at least partially surrounds magnets 44 within recess 49. Inner surface 51 may be formed with a generally smooth surface with no protrusions or other edges such that the profile of adhesive 46 thereby created also includes only a smooth surface with no protruding edges for patient comfort after removal of carrier 48 therefrom. In an exemplary embodiment, carrier 48 is formed of a water soluble material, such as polyvinyl alcohol (PVOH) or other water soluble polymer, for example. Carrier 48 may be formed of a material which does not bond with adhesive 46 and which may be removed from adhesive 46 after curing of adhesive 46.

In operation and referring to FIG. 8, the method of using magnetic orthodontic retainer system 40 will be described. To begin, recess 49 of carrier 48 is at least partially filled with adhesive 46. Adhesive 46 may be in the form of a viscous liquid at this stage and magnets 44 are at least partially embedded therein. Adhesive 46 fills recess 49 such that surface 47 of adhesive 46 substantially matches inner surface 51 of recess 49. At this point, adhesive 46 may optionally be partially cured, or pre-cured, with a suitable curing instrument, such as those described below, such that adhesive 46 is a highly viscous or substantially solid material, i.e., in a non-liquid state, to facilitate delivery to teeth 50*a*, 50*b*. Magnets 44, along with adhesive 46 and carrier 48, are releasably coupled by attractive forces to opposite sides of delivery member 42, as shown in FIG. 7A. Magnets 44, adhesive 46, and carrier 48 are not bonded to delivery member 42, rather, delivery member 42 functions to carry magnets 44 to their final destination on adjacent teeth. A release coating on delivery member 42, as described above, may further reduce the possibility of adhesive 46 or carrier 48 bonding to delivery member 42. A quantity of primer material (not shown), similar to primer material 18, described above with reference to FIG. 3, may be applied to a lingual surface of adjacent teeth 50*a*, 50*b* in a location where adhesive 46 will contact the lingual surface of teeth 50*a*, 50*b*.

Figure 9:
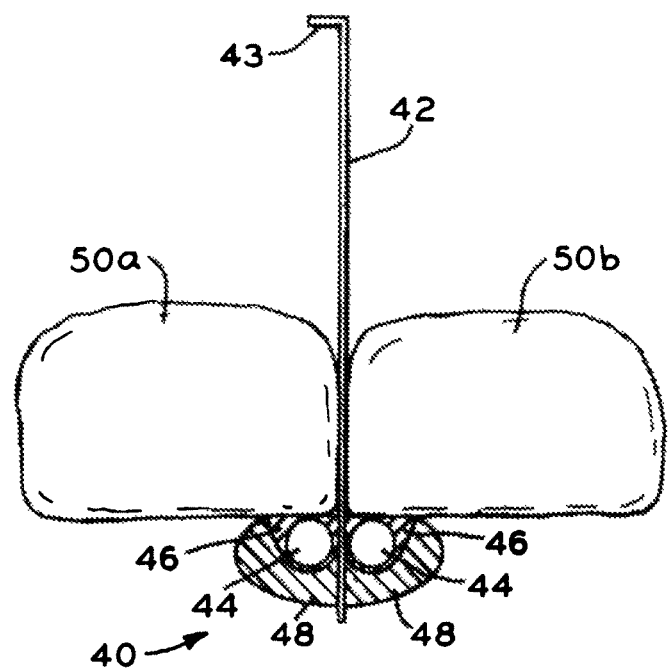

Delivery member 42, with magnets 44 carried thereon, is placed between a pair of adjacent teeth, for example, between teeth 50*a*, 50*b*. Delivery member 42 is then pulled via handle 43, for example, in the general direction of Arrow B (FIG. 8), as shown by delivery member 42 being pulled between teeth 50*a*, 50*b*. Arrow B generally indicates a direction away from the lingual side of the teeth and toward the facial side of the teeth. Delivery member 42 is pulled until adhesive 46 and/or magnets 44 contact the lingual surfaces of teeth 50*a*, 50*b*, as shown in FIG. 9.

Figure 10:
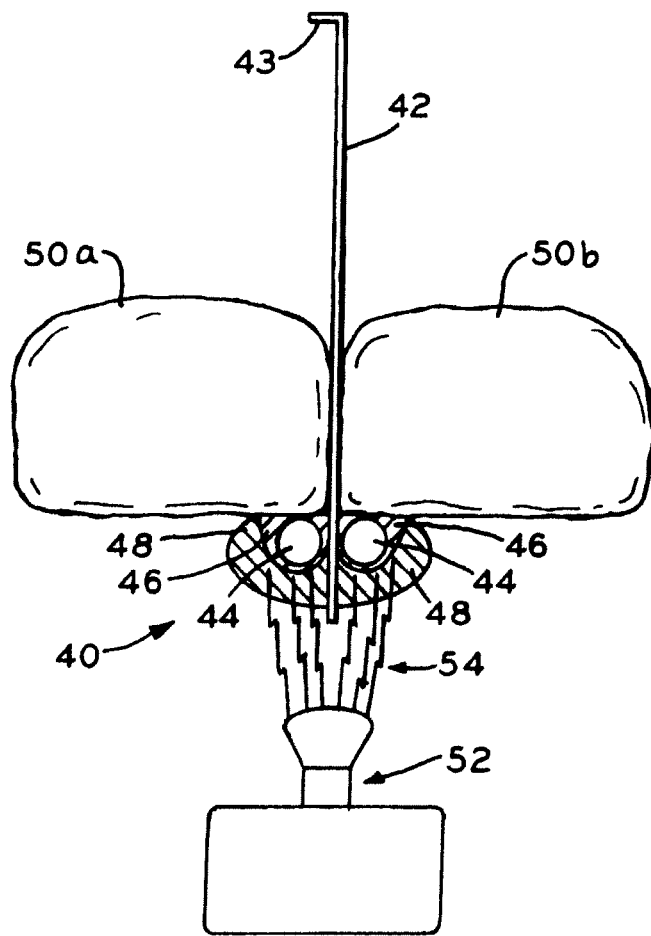

As shown in FIG. 10, adhesive 46 is then fully cured to completely harden adhesive 46 and thereby attach magnets 44 to teeth 50*a*, 50*b*. In one embodiment, curing instrument 52 may be used to cure adhesive 46 using curing rays 54. In an exemplary embodiment, curing rays 54 are light rays and curing instrument 52 is a light-based curing instrument. In one embodiment, the light rays are ultraviolet (UV) rays and the light-based curing instrument is a UV-based curing instrument. Examples of light-based curing instruments include the SmartLite®PS LED Curing Light and the Spectrum® 800 Curing Unit with Intensity Control, both available from DENTSPLY of York, Pa. Curing of adhesive 46 solidifies adhesive 46 and securely attaches adhesive 46 and magnets 44 to each of teeth 50*a*, 50*b*. Curing of adhesive 46 within recess 49 of carrier 48 ensures that adhesive 46 has a profile substantially matching inner surface 51 of recess 49. The profile of adhesive 46 advantageously has no edges or protrusions and provides a smooth and non-irritating lingual surface 47, as described further below.

Referring to FIG. 11, carrier 48 may be removed from adhesive 46 to reveal surface 47 which has a substantially smooth profile. Carrier 48 shown in FIG. 11 may be formed of a water soluble material, such as a water soluble polymer, i.e., polyvinyl alcohol (PVA or PVOH), for example. Water source 56 may supply an amount of water 58 or other water-based solution onto carrier 48. Water source 56 may be any suitable water supply instrument, such as the Waterpik® Dental Water Jet, available from Waterpik Technologies, Inc. of Newport Beach, Calif.; and the Interplak® Dental Water jet, available from Conair of Stamford, Conn., for example. Because carrier 48 is formed of a water-soluble material, application of water 58 dissolves carrier 48. As shown in FIG. 12, carrier 48 is partially dissolved. In one embodiment, suction may be applied adjacent water source 56 to remove water 58 and portions of carrier 48 which are dissolved. Carrier 48 may be formed of a material that is not harmful if swallowed.

Figure 13:
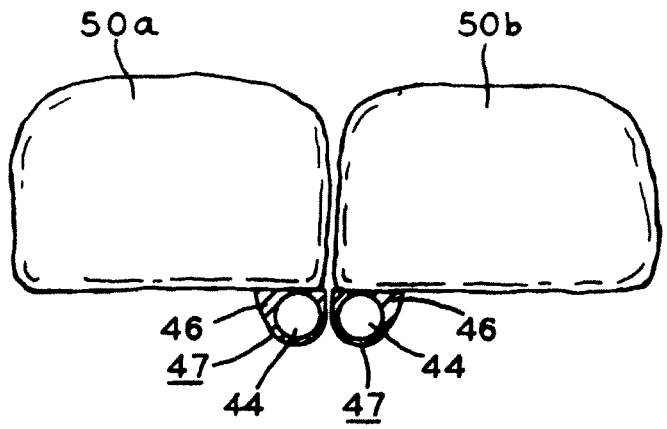

Referring to FIG. 13, further application of water 58 substantially and completely dissolves carrier 48 (FIGS. 11 and 12) such that adhesive 46 and magnets 44 are the only portion of system 40 to remain. Dissolving carrier 48 reveals a smooth lingual surface 47 of adhesive 46 defining a smooth profile of adhesive 46 which is completely cured to secure magnets 44 to teeth 50*a*, 50*b*. In an exemplary embodiment, lingual surface 47 of adhesive 46 is a substantially smooth surface with no sharp edges or projections. Such a smooth surface facilitates comfort for the patient. Advantageously, adhesive 46 requires no post-curing formation, such as by removing and/or manually forming adhesive 46 around magnets 44 to obtain a desired profile of adhesive 46, thereby greatly reducing the time needed for an orthodontist to apply magnets to a patient's dentition. For example, if the orthodontist has a large number of magnets to apply, system 40 greatly reduces the time required for such a procedure. The present method eliminates such post-curing formation and provides a fully cured and shaped profile for adhesive 46 which is both comfortable for a user of system 40 and is aesthetically pleasing. The shaped profile of adhesive 46 advantageously provides a comfortable retainer system for the patient and blends into the surrounding teeth proximate teeth 50*a*, 50*b*. Furthermore, adhesive 46 may be colored such that, when fully cured, adhesive 46 is substantially the same color as teeth 50*a*, 50*b* to which adhesive 46 is secured.

To complete the operation, delivery member 42 may be pulled and/or otherwise removed from between teeth 50*a*, 50*b*. Once delivery member 42 has been completely removed, magnets 44 with adhesive 46 remain attached to teeth 50*a*, 50*b*, for example, to provide an orthodontic retainer system, as shown in FIG. 13. Because magnets 44 and adhesive 46 are not secured to delivery member 42 and are only carried thereon via the mutual attraction between magnets 44, delivery member 42 simply slides between magnets 44 and adhesive 46 and the adjacent teeth to which adhesive 46 and magnets 44 are attached for removal of delivery member 42 from the mouth of the patient. Movement of delivery member 42 after curing of adhesive 46 will not disturb adhesive 46 and magnets 44 because the force coupling magnets 44 and adhesive 46 to delivery member 42 is less than the force adhering adhesive 46 and magnets 44 to the teeth. Once fixed in position, magnets 44 retain adjacent teeth without the need for other, more cumbersome orthodontic appliances. Although described above as removing delivery member 42 after removal of carrier 48, practice of the present method may alternatively involve removal of delivery member 42 first, followed by removal of carrier 48.

Figure 14:
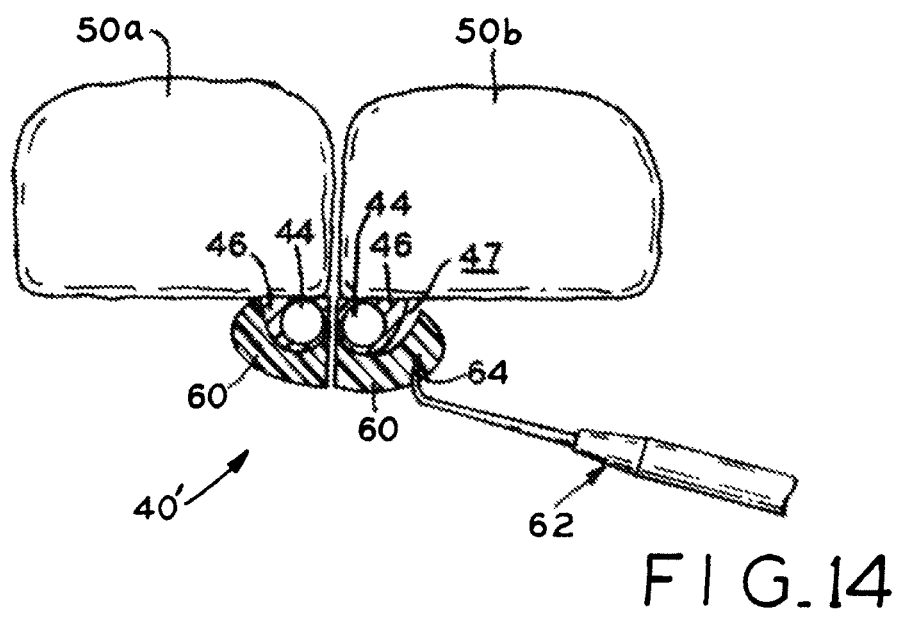

Referring to FIG. 14, an alternative embodiment retainer system 40' is shown and generally includes delivery member 42 with handle 43, magnets 44, adhesive 46, and carrier 60. Carrier 60 may be formed of a flexible material which does not bond with adhesive 46 and which may be removed from adhesive 46 after curing of adhesive 46. In an exemplary embodiment, carrier 60 is formed of a flexible silicone-based material which may be peeled off adhesive 46 using scaler 64 or another suitable dental instrument 62. Scaler 64 may pierce carrier 60 after which carrier 60 is peeled or pulled away from adhesive 46 to reveal the substantially smooth envelope or profile of adhesive 46, as described above. Alternatively, carrier 60 may be removed via any other instrument or by hand. For example, dental instrument 62 may include forceps which are used to grasp a portion of carrier 60 and remove carrier 60 to reveal the profile of adhesive 46.

Figure 21:
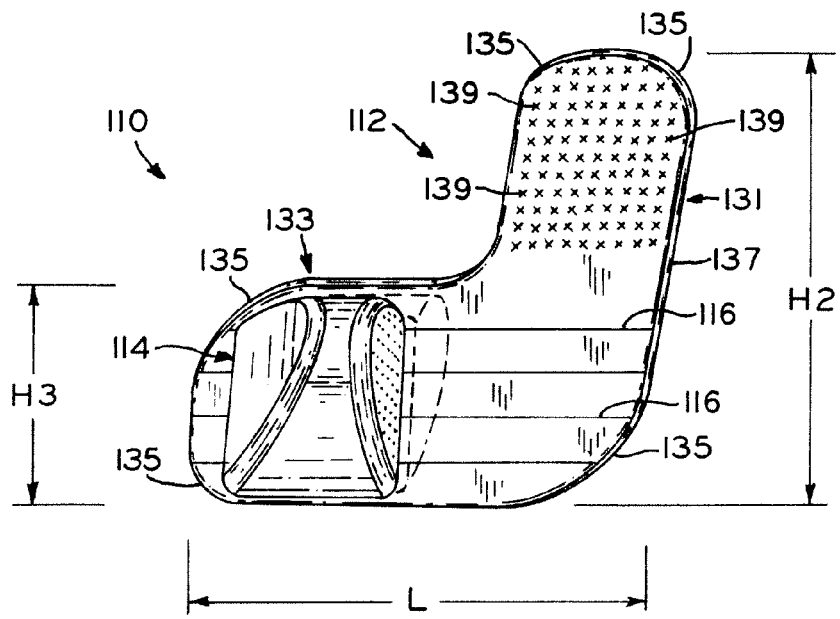
FIG. 21 is a perspective view of the delivery member of FIG. 19, further illustrating a pair of coupled mutually attractive members according to the embodiment of FIG. 15.

Referring now to FIG. 21, orthodontic retainer system 110 is shown, including strip or delivery member 112 and mutually attracted dental modules 114. While described and depicted herein with specific references to dental modules 114, delivery member 112 may also be used in conjunction with other dental modules described herein, such as dental modules 14 described above. Similarly, while described and depicted herein with specific references to delivery member 112, dental modules 114 may also be used in conjunction with other delivery members described herein, such as delivery member 12 described above. Mutually attracted dental modules 114 are releasably coupled by attractive forces to opposite sides of delivery member 112. For example, in one embodiment, each mutually attracted dental module 114 may comprise a magnet or any other suitable device capable of mutual attraction, i.e., electrostatic members. When mutually attracted dental modules 114 are magnets, they are coupled together on delivery member 112 via magnetic forces. Each mutually attracted dental module 114 has a dimension D3 (FIG. 18), such as a height, which may be as small as 0.010, 0.015, 0.020, or 0.025 inches (0.254 mm, 0.381 mm, 0.508 mm, or 0.635 mm) or as large as 0.030, 0.035, 0.040, or 0.045 inches (0.762 mm, 0.889 mm, 1.016 mm, or 1.143 mm), for example. In one exemplary embodiment, dimension D3 is 0.040 inches (1.016 mm).

Referring to FIGS. 15-18, in one exemplary embodiment, mutually attracted dental module 114 has a substantially polygonal or trapezoidal shape in cross-section taken along a direction perpendicular to tooth engaging surface 113, as best shown in FIG. 17. Specifically, tooth engaging surface 113, lingual surface 115, and bottom surface 117 are substantially planar surfaces. Curved top surface 119, in conjunction with rounded and/or chamfered corners 121, joins each of tooth engaging surface 113, lingual surface 115, and bottom surface 117 to one another. Additionally, dental module 114 has a width W (FIG. 18) that corresponds to the distance between opposing ends of bottom surface 117. Similarly, the radius of curvature of top surface 119 corresponds to the width of dental module 114 and extends between the opposing ends of bottom surface 117. In one exemplary embodiment, the radius of curvature of top surface 119 is 0.040 inches (1.016 mm). However, the radius of curvature of top surface 119 may be as small as 0.020, 0.025, 0.030, or 0.035 inches (0.508 mm, 0.635 mm, 0.762 mm, 0.889 mm) or as large as 0.040, 0.045, 0.050, or 0.055 inches (1.016 mm, 1.143 mm, 1.27 mm, or 1.397 mm), for example. In one exemplary embodiment, lingual surface 115 forms an angle α with the apex of top surface 119. In one exemplary embodiment, angle α is approximately 45 degrees. However, angle α may be as small as 20, 25, 30, 35, or 40 degrees or as large as 45, 50, 55, 60, and 65 degrees, for example. Advantageously, by angling lingual surface 115 and utilizing rounded corners 121, the comfort of the patient is facilitated, and the patient may floss between adjacent teeth on which dental modules 114 are attached without cutting the floss.

In another exemplary embodiment, tooth engaging surface 113 is modified to facilitate the retention of an adhesive thereon. For example, tooth engaging surface 113 may include a grid, mesh, or series of geometric undercuts to provide an abrasive surface to which adhesive 16, 46 (FIG. 24) is applied. In another exemplary embodiment, tooth engaging surface 113 may be roughened, or may include a coating formed by chemical vapor deposition (CVD). Each mutually attracted dental module 114 is made of a biocompatible material to allow its implantation in the mouth for a period of time. For example, referring to FIGS. 17 and 18, in one exemplary embodiment, each mutually attracted dental module 114 has an outer coating 123, such as gold-plating, substantially entirely surrounding inner magnet 129. In one exemplary embodiment, inner magnet 129 is comprised of a permanent magnet, such as a rare-earth magnet. In one exemplary embodiment, inner magnet 129 is a neodymium-iron-boron magnet. In another exemplary embodiment, module 114 lacks outer coating 123.

Figures 19, 20:
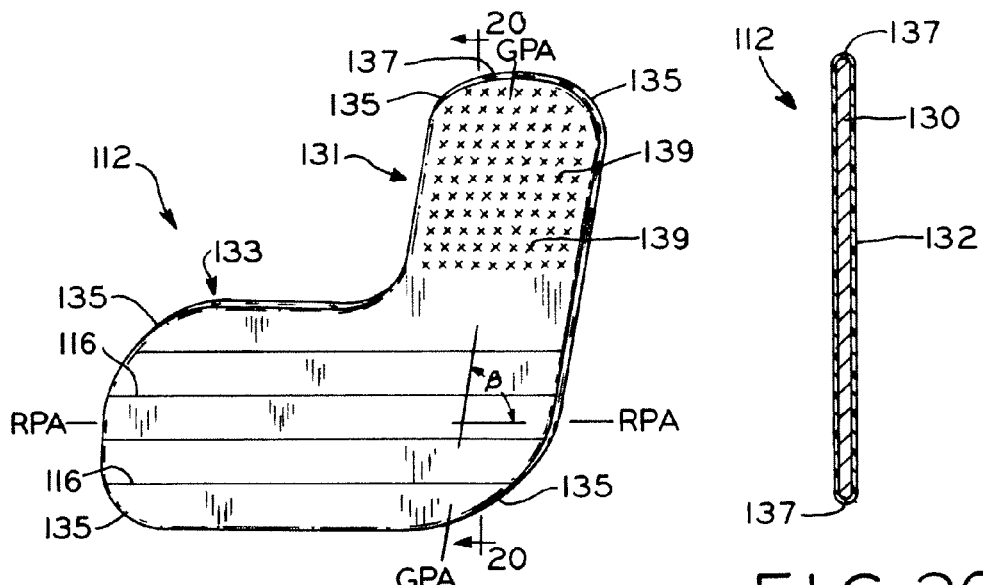
FIG. 19 is a perspective view of a delivery member according to another exemplary embodiment.
FIG. 20 is a cross-sectional view of the delivery member of FIG. 19 taken along line 20-20 of FIG. 19.

Referring to FIGS. 19-21, delivery member 112 may be substantially similar to delivery member 12, described above with reference to FIGS. 1-3, except as described below. For example, delivery member 112 may also be formed of a flexible plastic material, such as Mylar® material, for example, or, alternatively, a metal material, such as stainless steel, for example. In one embodiment, delivery member 112 includes core 130, formed from a material described above, and release coating 132 substantially surrounding core 130. For example, release coating 132 may be a silicone, polyethylene, or fluoropolymer coating, such as polytetrafluoroethylene (PTFE) which is commercially available as Teflon® from E. I. du Pont de Nemours and Company of Wilmington, Del.; Silicon Premium, a siloxane release coating commercially available from General Electric Company of Waterford, N.Y.; and Clearsil® fluorosilicone release films and ClearLES™ silicone release liners commercially available from CPFilms, Inc. of Martinsville, Va.

Additionally, as shown in FIGS. 19-21, delivery member 112 has a substantially L-shape including gripping portion 131 and retention portion 133. Longitudinal gripping portion axis GPA intersects longitudinal retention portion axis RPA to form the substantially L-shape, wherein the intersection of longitudinal gripping portion axis GPA and longitudinal retention portion axis RPA results in the formation of angle β. In one exemplary embodiment, angle β is equal to 90 degrees or is any acute angle greater than 30 degrees and less than 90 degrees. As shown in FIG. 19, in one exemplary embodiment, angle β is 80 degrees. Additionally, to facilitate patient comfort during the delivery of dental modules 114, gripping portion 131 and retention portion 133 have rounded and/or chamfered corners 135. In one exemplary embodiment, shown in FIG. 20, periphery 137 of delivery member 112 also has a bulbous or rounded shape to further facilitate patient comfort during the delivery of dental modules 114. Gripping portion 131 may also include a grid, mesh, or series of geometric undercuts 139, shown in FIG. 19, to provide an abrasive surface upon which a orthodontist may grasp either directly by hand or indirectly through the use of dental instruments.

Delivery member 112 has a height H2 that may be a small as 0.25, 0.30, 0.35 or 0.40 inches (6.35 mm, 7.62 mm, 8.89 mm, 10.16 mm) or as large as 0.45, 0.50, 0.75, or 1.00 inches (11.43 mm, 12.7 mm, 19.05 mm, or 25.4 mm), for example. The length of delivery member 112 can be any size to facilitate easy access for an orthodontist for pulling delivery member 112 between a pair of adjacent teeth 20a and 20b, as described in detail below. In exemplary embodiments, delivery member 112 may have a length L as small as 0.25, 0.30, 0.35 or 0.40 inches (6.35 mm, 7.62 mm, 8.89 mm, 10.16 mm) or as large as 0.45, 0.50, 0.75, or 1.00 inches (11.43 mm, 12.7 mm, 19.05 mm, or 25.4 mm), for example. Additionally, retention portion 133 of delivery member 112 has a height H3. In exemplary embodiments, height H3 of retention member 133 is as small as 0.10, 0.15, 0.20 or 0.25 inches (2.54 mm, 3.81 mm, 5.08 mm, or 6.35 mm) or as large as 0.30, 0.35, 0.40, or 0.45 inches (7.62 mm, 8.89 mm, 10.16 mm, or 11.43 mm), for example. In an alternative embodiment, delivery member 112 may be part of a continuous piece of material which has pairs of mutually attracted dental modules 114 carried thereon at various spaced distances and may operate in the same manner as described in detail above with reference to delivery member 12. Further, delivery member 112 may also include scribe marks 116, shown in FIGS. 19 and 21, which may be lettered or numbered accordingly to provide a depth gauge, thereby providing the orthodontist with an indication of the depth of delivery member 112 with respect to adjacent teeth 22.

Except as described below, the method of applying magnetic orthodontic retainer system 110 is similar to the method described above for applying magnetic orthodontic retainer systems 10, 10". Referring now to FIGS. 22-27, the mutual attraction of mutually attracted dental modules 114 retains both modules 114 in place on delivery member 112. A quantity of adhesive 16, 46, described in detail above, is then placed on tooth engaging surface 113 of dental modules 114. In another exemplary embodiment, adhesive 16, 46 may be placed on dental modules 114 prior to retaining dental modules 114 on delivery member 112. Alternatively, adhesive 16, 46 may be applied directly to adjacent teeth, such as teeth 22, i.e., teeth 22a and 22b. Furthermore, in one exemplary embodiment, primer material 18 (FIG. 3) is applied to a posterior surface of adjacent teeth 22, i.e., teeth 22a and 22b, in a location where adhesive 16, 46 applied to dental modules 114 will contact the surface of teeth 22a and 22b. Primer material 18 may comprise a material such as acid for etching a posterior surface of each tooth 22. Primer material 18 may also comprise chemical etching or any type of material to facilitate bonding with adhesive 16, 46.

Figure 28:
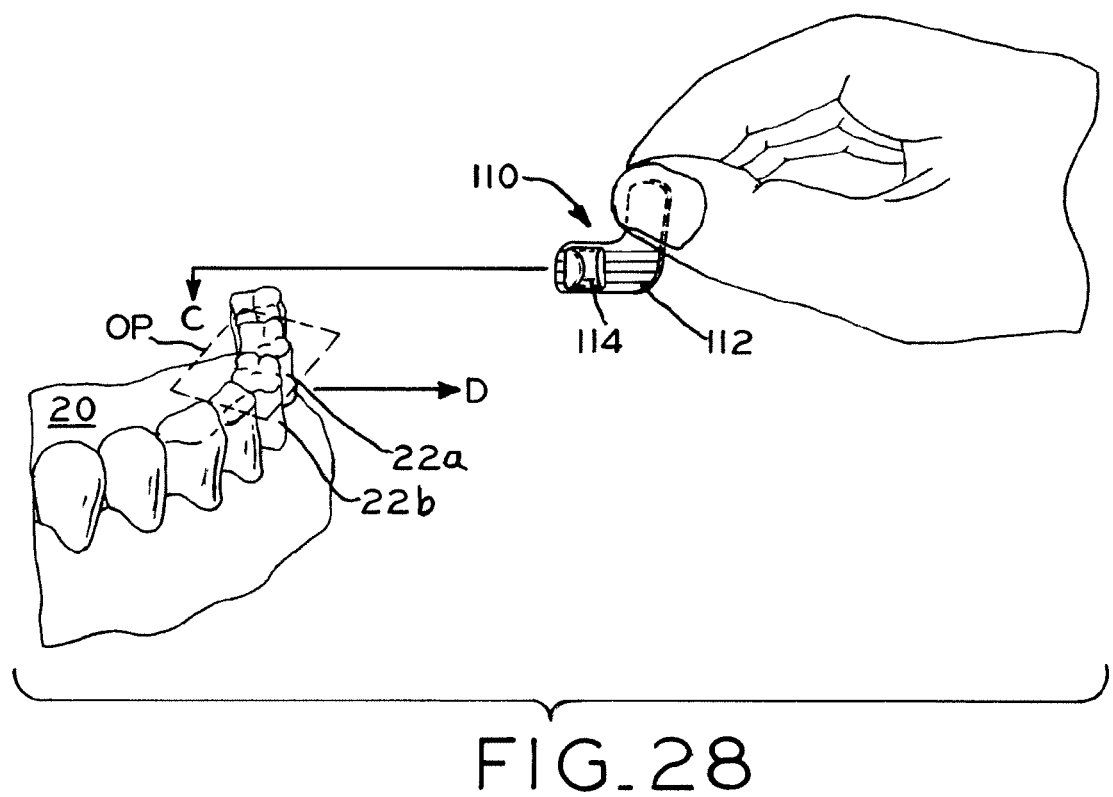
FIG. 28 is a perspective view of a portion of a patient's mouth, further depicting a partial perspective view of an orthodontist's hand grasping the delivery member of FIG. 19 having a mutually attractive member according to FIG. 15 positioned thereon.

Similar to the method described above, delivery member 112, with mutually attracted dental modules 114 carried thereon, is placed between a pair of adjacent teeth, for example, between teeth 22a and 22b. Referring to FIG. 28, in one exemplary embodiment, the orthodontist grasps gripping portion 131, either directly by hand or indirectly with an orthodontic instrument, and positions retention portion 133 between teeth 22a and 22b, while the orthodontist's fingers and/or the instrument remain substantially outside the oral cavity and more specifically, outwardly of occlusal plane OP defined by the occlusal surfaces of teeth 22a and 22b. Stated another way, the orthodontist's fingers and/or the instrument remain on a side of occlusal plane OP disposed opposite the teeth. Specifically, referring to FIG. 28, the orthodontist moves delivery member 112 inwardly into the patient's oral cavity and then downwardly between teeth 22a and 22b, as shown by Arrow C. Delivery member 112 is then pulled outwardly or facially in the general direction of Arrow D, resulting in delivery member 112 being pulled between teeth 22a and 22b. During movement of delivery member 112, the orthodontist's fingers and/or instrument remain substantially outside the patient's oral cavity and outwardly of occlusal plane OP of teeth 22a and 22b, as described above. Delivery member 112 is pulled until tooth engaging surfaces 113 of dental modules 114 contact adjacent teeth. At this point, adhesive 16, 46 contacts primer material 18. Adhesive 16, 48 may then be cured to harden adhesive 16, 46 and attach dental modules 114 to teeth 22. In one embodiment, an ultraviolet or visible light source, such as those described in detail above with reference to adhesive 46, may be used to cure adhesive 16, 46.

To complete the operation, delivery member 112 is pulled further outwardly or facially to remove delivery member 112 from between teeth 22a and 22b. Due to the substantially L-shape of delivery member 112, the need for the orthodontist to manipulate or otherwise move and/or grasp the patient's lip, tongue, and/or cheek to facilitate removal of delivery member 112 is substantially eliminated. Once delivery member 112 has been completely removed, mutually attracted dental modules 114 remain attached to teeth 22a and 22b to provide an orthodontic retainer and, in most cases, the mutually-facing surfaces of modules 114 engage each other to aid in retaining the positions of the teeth.

Because modules 114 are not secured to delivery member 112 and are only carried thereon via the mutual attraction between mutually attracted dental modules 114, delivery member 112 simply slides between the adjacent teeth for removal of delivery member 112 from mouth 20 (FIG. 2). Movement of delivery member 112 after curing will not disturb dental modules 114 because the force coupling dental modules 114 to delivery member 112 is less than the force adhering dental modules 114 and adhesive 16, 46 to the teeth. Once placed, mutually attracted dental modules 114 retain adjacent teeth without the need for other, more cumbersome orthodontic appliances. In another exemplary embodiment, orthodontic retainer system (not shown) may include capsules 24 or the capsules made of mutually attractive material, as described in detail herein.

Although orthodontic retainer systems 110 have been shown and illustrated herein as being applied to adjacent teeth in the lower portion of the mouth, i.e., to teeth in the mandibular arch, the systems may of course be applied to adjacent teeth in the upper portion of the mouth, i.e., to teeth in the maxillar arch, by simply inverting delivery member 112 and dental modules 114. Furthermore, in an alternative embodiment (not shown), orthodontic retainer systems 110 may be applied in any position on adjacent teeth as opposed to the lingual position as described and illustrated herein.

The method of application for orthodontic retainer systems 110 described above may also be used in an alternative, indirect application. In an alternative embodiment, orthodontic retainer system 110 is applied to an identical, non-human version of mouth 20, for example, a formed mold of mouth 20 including teeth 22. Orthodontic retainer system 110 is applied to the formed mold of teeth 22 in an identical fashion as described above. After application to the mold, an orthodontist could use any indirect technique commonly known by the dental profession to simultaneously remove all capsules 24 and/or modules 14, 114 and simultaneously apply all capsules 24 and/or modules 14, 114 in the corresponding patient's mouth 20. All capsules 24 and/or modules 14, 114 may be included in a delivery tray or elastic material having the capability to simultaneously move all capsules 24 and/or modules 14, 114 from the mold to mouth 20.

Referring to FIGS. 29-44, further concepts in accordance with additional embodiments of the present invention are shown, including a dental or retainer module 210, shown in FIGS. 29-35, and a delivery member 212, shown in FIGS. 36-40, together with a method of applying retainer modules 210 to a pair of adjacent teeth using delivery member 212, as shown in FIGS. 36-43B.

Figure 29:
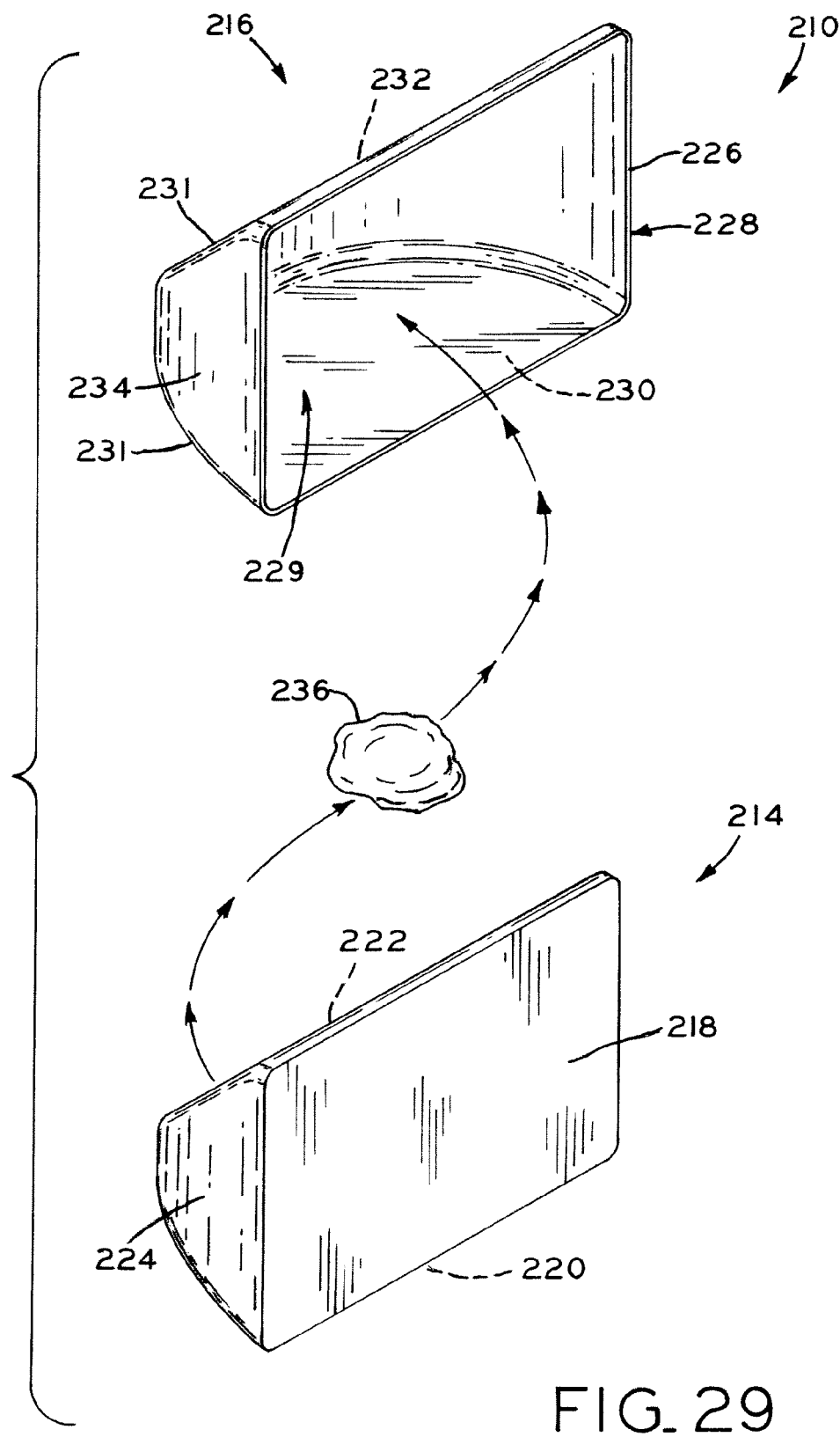
FIG. 29 is a perspective exploded view showing a magnet and a cover member of a retainer module of a further embodiment.

Referring to FIG. 29, retainer module 210 generally includes a magnet 214 and an enclosure or cover member 216. Magnet 214 has a shape very similar to that of dental module 114 shown in FIGS. 15-18 and described above, including a generally trapezoidal profile with a planar tooth-facing bonding surface 218, shown as substantially rectangular. Magnet 214 further includes a planar interproximal surface 220 having a semicircular shape, a planar lingual surface 222 disposed at an angle with respect to tooth-facing surface 218 and interproximal surface 220, and a curved or arched lingual surface 224 that curves around the semicircular profile of interproximal surface 220 and connects bonding surface 218, interproximal surface 220, and planar lingual surface 222.

Magnet 214 may be a permanent magnet made from any magnetic material, such as a magnet made from an alloy of a rare earth element. For example, magnet 214 may be a neodymium magnet, i.e., made from a neodymium/iron/boron alloy, or may be made from other alloys of rare earth elements, such as a samarium-cobalt magnet, for example. Magnet 214 may have an exterior coating 225 (FIG. 35) of a biocompatible metal, such as gold, titanium, or tantalum, for example, that may be applied via a process such as immersion coating, chemical vapor deposition (CVD) physical vapor deposition (PVD), electroplating, or sputtering/vacuum deposition. Coating 225 may have a thickness of between 0.0002 inches and 0.0005 inches (between 0.0051 mm and 0.0127 mm), for example. In one embodiment, magnet 214 is a neodymium/iron/boron magnet having a gold coating 225 applied as two successive layers via electroplating. Coating 225 completely covers magnet 214, and prevents exposure of the material of the permanent magnet to the oral cavity of a patient.

Referring additionally to FIGS. 30-34, cover member 216 is shown in detail and in one embodiment, has a shape analogous to that of magnet 214, including a rim 226 defining an open end 228 of cover member 216 having a rectangular shape corresponding to, and sized slightly greater than, bonding surface 218 of magnet 214. Open end 228 provides access to the open interior 229 of cover member 216. Cover member 216 additionally includes an interproximal surface 230, a planar lingual surface 232, and a curved lingual surface 234 that are each sized slightly greater than, and which correspond to, interproximal surface 220, planar lingual surface 222, and curved lingual surface 224 of magnet 214, respectively. Curved or radiused edges 231 connect the foregoing surfaces. In one embodiment, the walls of cover member 216 that correspond to each of the foregoing surfaces have a thickness of 0.0048 inches (0.122 mm).

Cover member 216 may be made of a relatively hard, wear resistant biocompatible metal, such as stainless steel, and provides an enclosure for magnet 214 for sealing magnet from the oral cavity of a patient. Cover member 216 also protects magnet 214 from wear, yet allows passage of the magnetic field forces of magnet 214 through cover member 216. In one embodiment, cover member 216 is made from a substantially non-magnetic stainless steel, such as a 300 series stainless steel.

Figure 32:
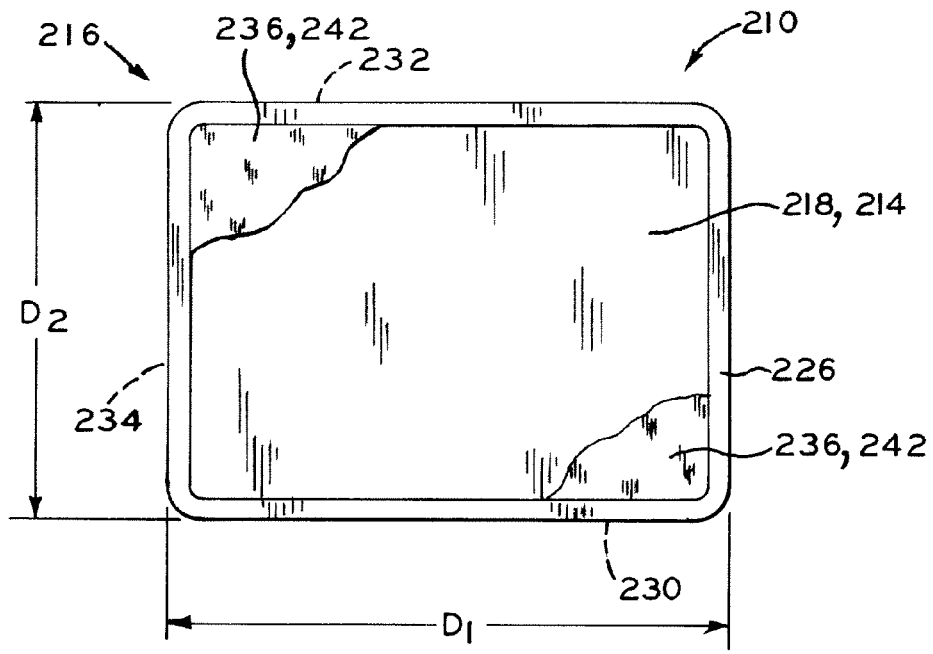
FIG. 32 is a front view of the retainer module.
Figure 34:
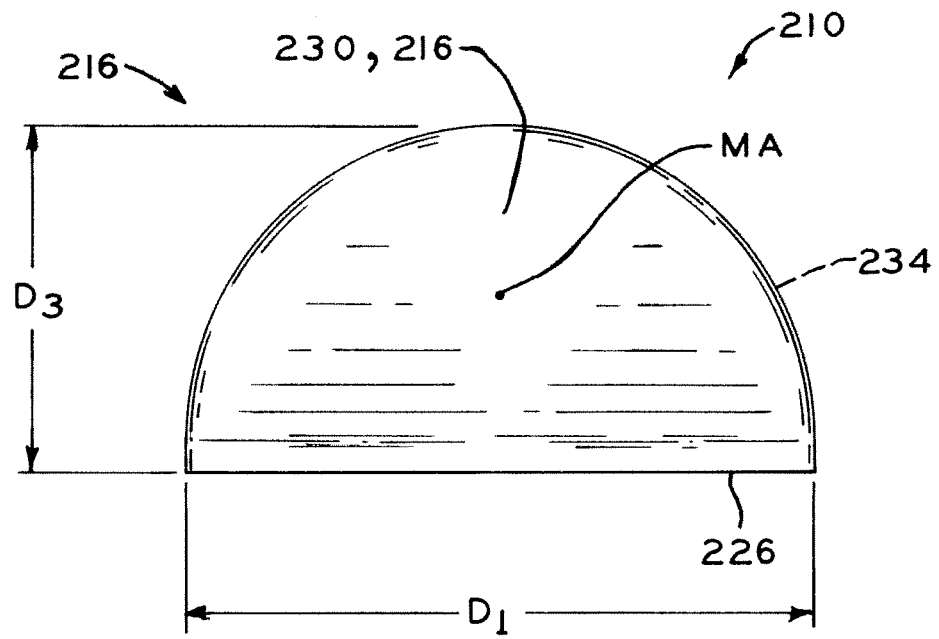
FIG. 34 is a bottom view of the retainer module.

Exemplary dimensions for cover member 216, which are also the overall dimensions of retainer module 210, are set forth below. These dimensions also generally correspond to those of magnet 214 in that the dimensions of cover member 216 will be only slightly greater than the dimensions of the corresponding surfaces of magnet 214 which, in one embodiment, may be sized to fit closely within cover member 216 as described below. Referring to FIGS. 32 and 34, rim 226 of cover member 216 is disposed around bonding surface 218 of magnet 214, and has a planar profile with a long dimension $D_1$ which, in one embodiment, is 0.080 inches (2.032 mm) and, in other embodiments, may be as little as 0.040 inches or 0.060 inches (1.016 mm or 1.524 mm), or as great as 0.10 inches or 0.120 inches (2.54 mm or 3.048 mm), for example. Rim 226 also has a short dimension $D_2$ which, in one embodiment, is 0.060 inches (1.524 mm) and, in other embodiments, may be as little as 0.040 inches or 0.05 inches (1.016 mm or 1.27 mm), or as great as 0.070 inches or 0.08 inches (1.778 mm or 2.032 mm), for example.

As shown in FIG. 34, interproximal surface 230 is planar and semicircular shaped, and has dimension $D_1$ as well as a dimension $D_3$ corresponding to the radius of its semicircular shape and which, in one embodiment, is 0.050 inches (1.27 mm) and, in other embodiments, may be as little as 0.030 or 0.040 inches (0.762 mm or 1.016 mm) or as great as 0.060 or 0.070 inches (1.524 mm or 1.778 mm), for example.

Figure 33:
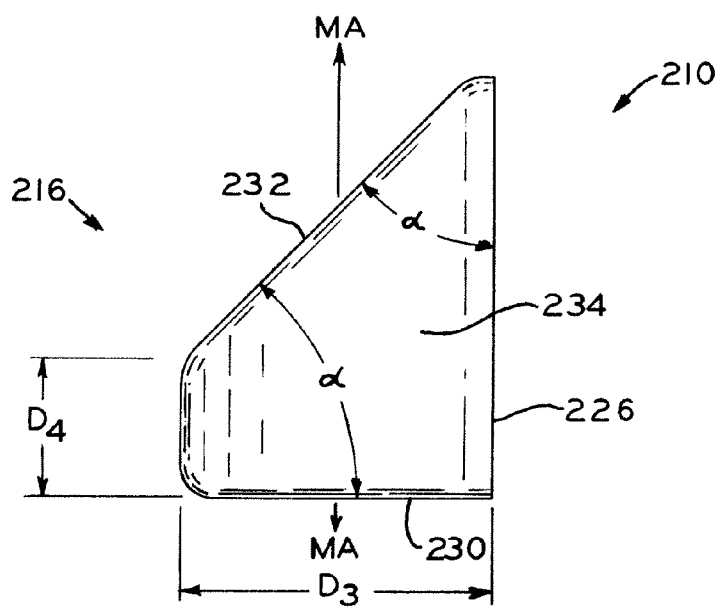
FIG. 33 is a side view of the retainer module.

Curved lingual surface 234 is curved around the semicircular shape of interproximal surface 230, and has a dimension $D_4$ between the apex of its curve around planar lingual surface 232 and interproximal surface 230, shown in FIG. 33 and which, in one embodiment, is 0.020 inches (0.508 mm) and, in other embodiments, may be as little as 0.010 inches (0.254 mm) or as great as 0.030 inches 0.762 mm), for example.

Figure 31:
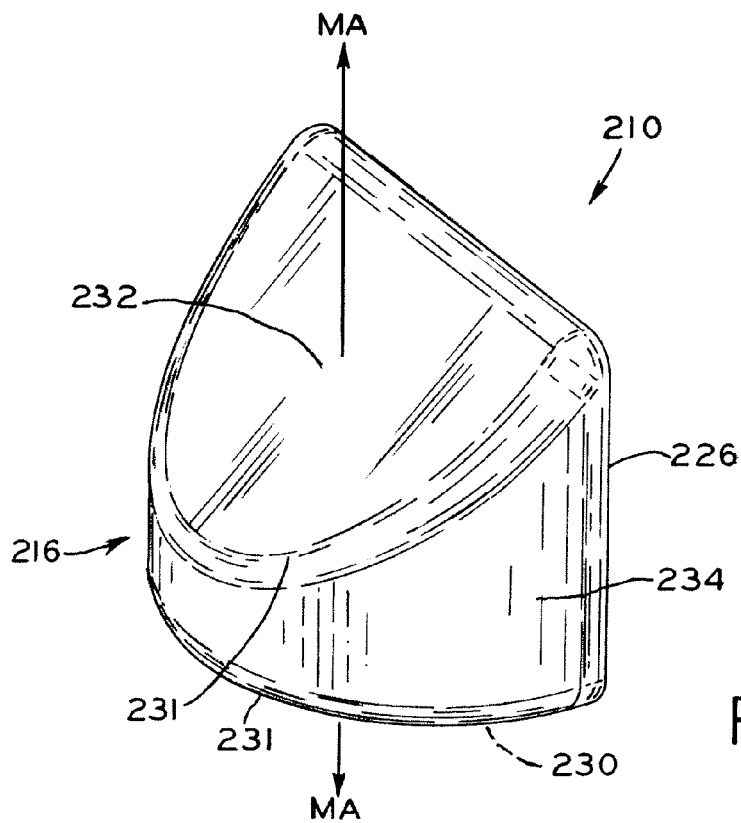
FIG. 31 is a rear perspective view of the retainer module.

As shown in FIGS. 31 and 33, planar lingual surface 232 is angled or sloped at an angle $\alpha$ with respect to either a plane defined by rim 226 and/or with respect to contact surface 222 which, in one embodiment, is 45 degrees. However, in other embodiments, angle $\alpha$ may be as small as 20, 25, 30, 35, or 40 degrees or as large as 45, 50, 55, 60, and 65 degrees, for example, with respect to either the plane defined by rim 226, or interproximal surface 230. Planar lingual surface 232 also has dimension $D_1$ where same merges with rim 226. When a pair of retainer modules 210 are applied to their respective teeth, the sloped or angled planar lingual surface 232 and the curved lingual surface 234 of the modules are exposed to the oral cavity, and the geometric shapes of these surfaces, together with the radiused or chamfered edges 231 between these surfaces, facilitates patient comfort by providing a smooth and minimized profile to the patient's tongue which also resists retention of food particles to promote oral hygiene.

The edges 231 respectively disposed between rim 226, interproximal surface 230, planar lingual surface 232, and curved lingual surface 234 are smoothly curved or radiused, and may have a radius of curvature between 0.004 and 0.010 inches (0.1016 mm and 0.254 mm), for example. Alternatively, edges 231 may be chamfered.

Referring to FIG. 29, to assemble retainer module 210, an amount of a suitable adhesive 236, such as one of those described above, is placed within the open interior 229 of cover member 216, and magnet 214 is then inserted through open end 228 of cover member 216 with the cooperating surfaces of magnet 214 and cover member 216, described above, aligning with one another such that magnet 214 is seated within the open interior 229 of cover member 216. Upon seating of magnet 214 within cover member 216, adhesive 236 will spread around magnet 214 between the external surfaces of magnet 214 and the internal surfaces of cover member 216 to form a relatively uniform layer 240 of adhesive 236, shown in FIG. 35, between the external surfaces of magnet 214 and the internal surfaces of cover member 216.

Figure 30:
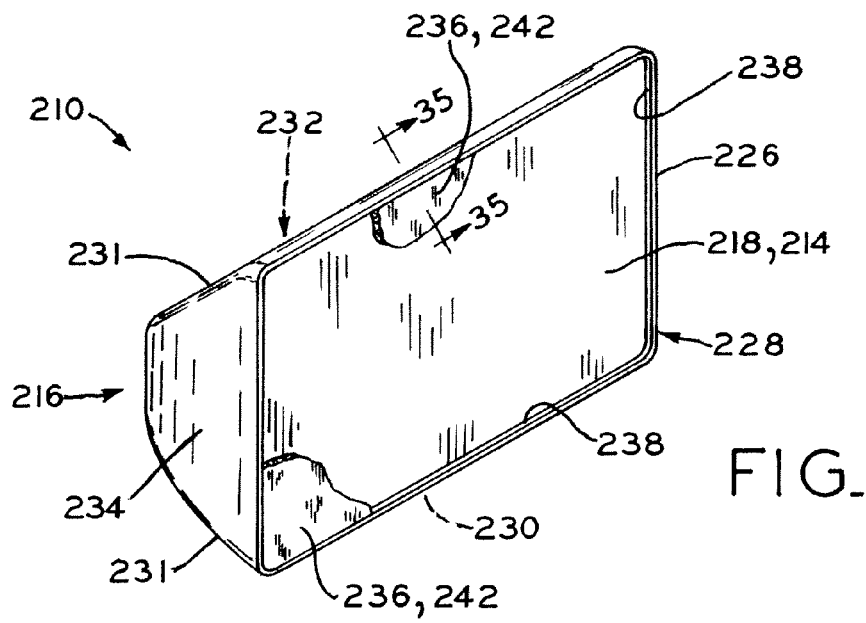
FIG. 30 is a front perspective view of the retainer module.
Figure 35:
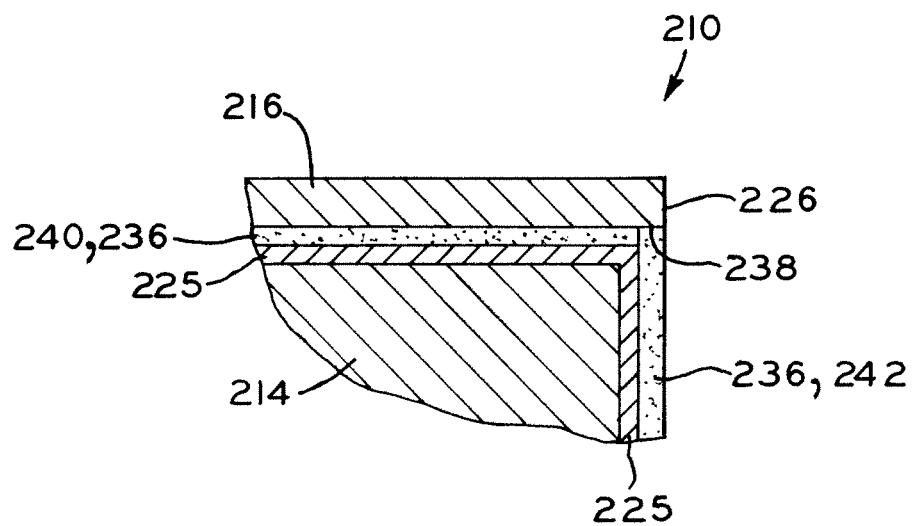
FIG. 35 is a sectional view taken along line 35-35 of FIG. 30.

As shown in FIGS. 30, 32, and 35, an additional amount of adhesive 236 may be applied across open end 228 of cover member 216 to bonding surface 218 of magnet 214 generally within rim 226 of cover member 216. As shown in FIGS. 30 and 35, rim 226 may be dimensioned to provide a small recess 238 within open end 228 of cover member 216 across bonding surface 218 of magnet 214. A layer or cap 242 of adhesive 236 may be placed within recess 238 and leveled off by a suitable instrument such as a spatula (not shown) to close open end 228 of cover member 216 across the face of bonding surface 218 of magnet 214. Only a portion of this layer or cap 242 of adhesive 236 is shown in FIGS. 30 and 32, it being understood that the adhesive will typically completely cover bonding surface 218 of magnet 214.

Then, the adhesive 236 may be cured in suitable manner, such as by exposure to ultraviolet light, by a chemical reaction, or by heating, depending upon the type of adhesive used. The curing of the adhesive 236 of layer 240 forms a tight bond between the external surfaces of magnet 214 and the internal surfaces of cover member 216 to secure magnet 214 within cover member 216 and form a retainer module 210 as a substantially integral or unitary structure. The adhesive 236 within recess 238 across the bonding surface 218 of magnet 214 provides a layer or cap 242 of adhesive that closes the interior of cover member 216 such that magnet 214 is effectively encapsulated and sealed within cover member 216.

In other embodiments, adhesive 236 is not applied within recess 238 across the bonding surface 218 of magnet 214, or cover member 216 may lack recess 238 such that rim 226 is dimensioned to be flush with tooth-facing surface 218 of magnet, such that bonding surface 218 remains exposed to the exterior of retainer module 210, with the remaining surfaces between magnet 214 and cover member 216 occupied by layer 240 of adhesive 236 to thereby seal magnet 214 within cover member 216 with the bonding surface 218 of magnet 214 uncovered by adhesive and directly exposed.

Bonding surface 218 of magnet 214 may optionally be roughened, or provided with rough or porous surface features, or a rough or porous coating, for example, in order to enhance the ability of adhesive 236 to bond thereto. By contrast, the outer surfaces of cover member 216, described above, will typically be smooth.

In this manner, as best shown in FIG. 35, each retainer module 210 includes, when viewed in cross section, a layered structure including the material of magnet 214, the biocompatible coating 225 of magnet, layer 240 of adhesive 236, and cover member 216. Advantageously, the material of magnet 214 is sealed from, and prevented from coming into contact with, the oral cavity of a patient by a double enclosure or double encapsulation structure, including coating 225 of magnet 214 and the enclosure or encapsulation provided by cover member 216 and adhesive 236.

The poles of magnet 214 are oriented such that the primary direction of magnetization, i.e., its magnetic moment, is along a magnetization axis MA-MA that is disposed parallel to bonding surface 218 of magnet 214 and extends centrally through interproximal surfaces 220 and 230 of magnet 214 and cover member 216 and planar lingual surfaces 222 and 232 of magnet 214 and cover member 216, respectively, as shown in FIGS. 31, 33, and 34. The poles of a pair of such magnets 214 are oppositely oriented, with the force of attraction between the magnets 214 of a pair of retainer modules 210 is sufficient to hold the modules 210 tightly together with their respective planar interproximal surfaces 230 in engagement with one another, with the magnetic attraction force transmitted through coatings 225 of magnets 214 and through cover members 216. As discussed below, when interproximal surfaces 230 of a pair of retainer modules 210 are magnetically coupled on opposite sides of delivery member 212, the magnetization axes MA-MA of retainer modules 210 will tend to automatically rotationally and positionally align retainer modules 210 such that their tooth-facing surfaces 218 are parallel to one another.

Figure 44:
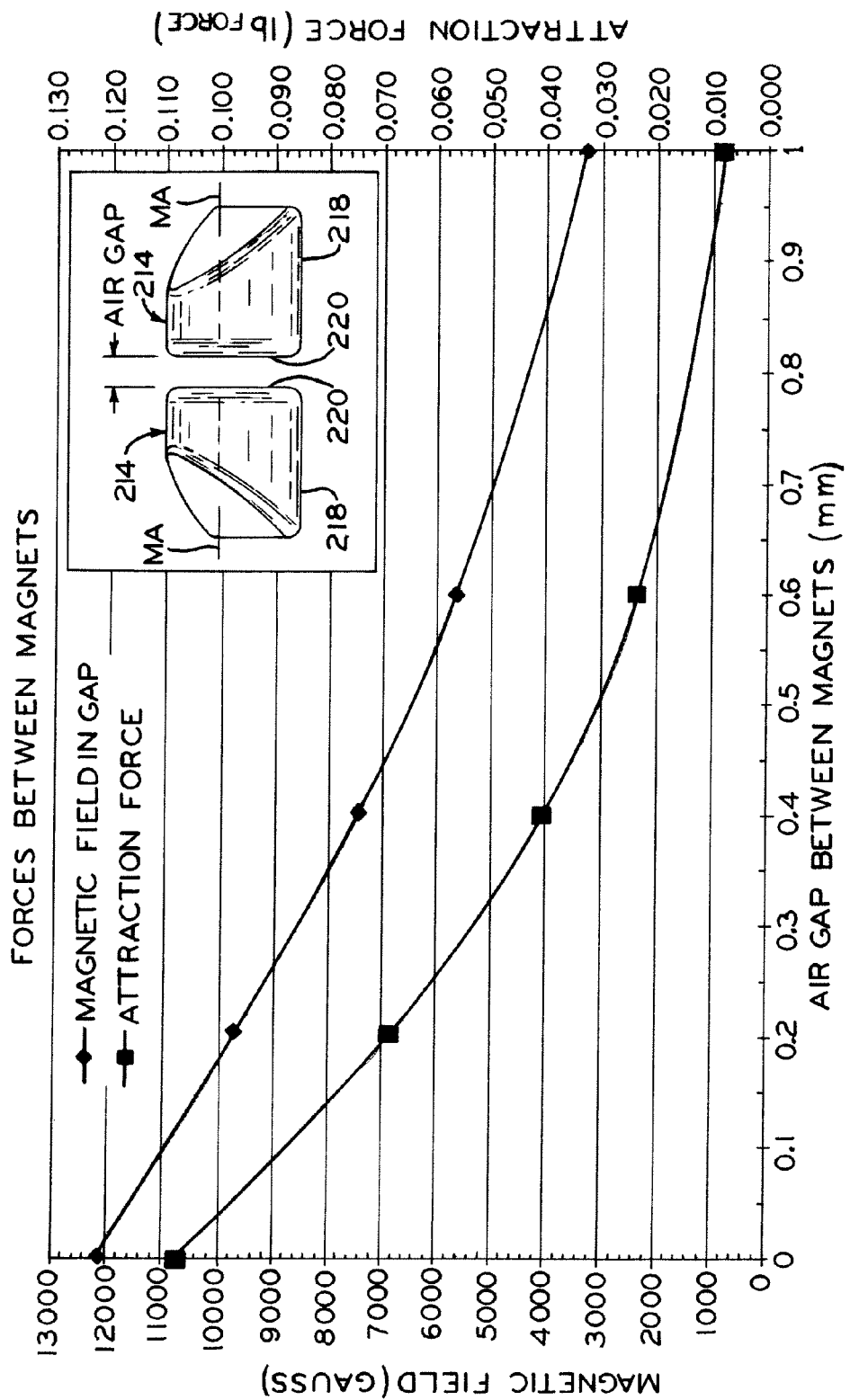
FIG. 44 is a chart of magnetic field and attraction forces vs. the air gap or separation distance between the magnets of the retainer modules.

Referring to FIG. 44, a chart showing the calculated magnetic field strength and magnetic attraction force between a pair of magnets 214 is shown as a function of the air gap, or effective separation distance, between interproximal surfaces 220 of a pair of magnets 214. When the interproximal surfaces 230 of a pair of modules 210 are magnetically engaged in the manner discussed below, the separation distance between the interproximal surfaces 220 of their respective magnets 214 will be twice the thickness of the wall of each of the cover members 216 of module 210. Thus, if this thickness is 0.0048 inches (0.122 mm), the air gap will be 0.0096 inches (0.244 mm) which, referring to FIG. 44, corresponds to a magnetic field density of about 9,000 gauss and an magnetic attraction force of about 0.060 lbs. of force (27.2 g-force, 0.27 N). Generally, the material of magnets 214, the size of magnets 214, and the separation between the magnets 214 when in use, i.e., the thickness of the walls of cover members 216, are the principal variables that may be selected to provide a desired magnetic force for retaining a pair of teeth with respect to one another in the manner described below.

Figure 36:
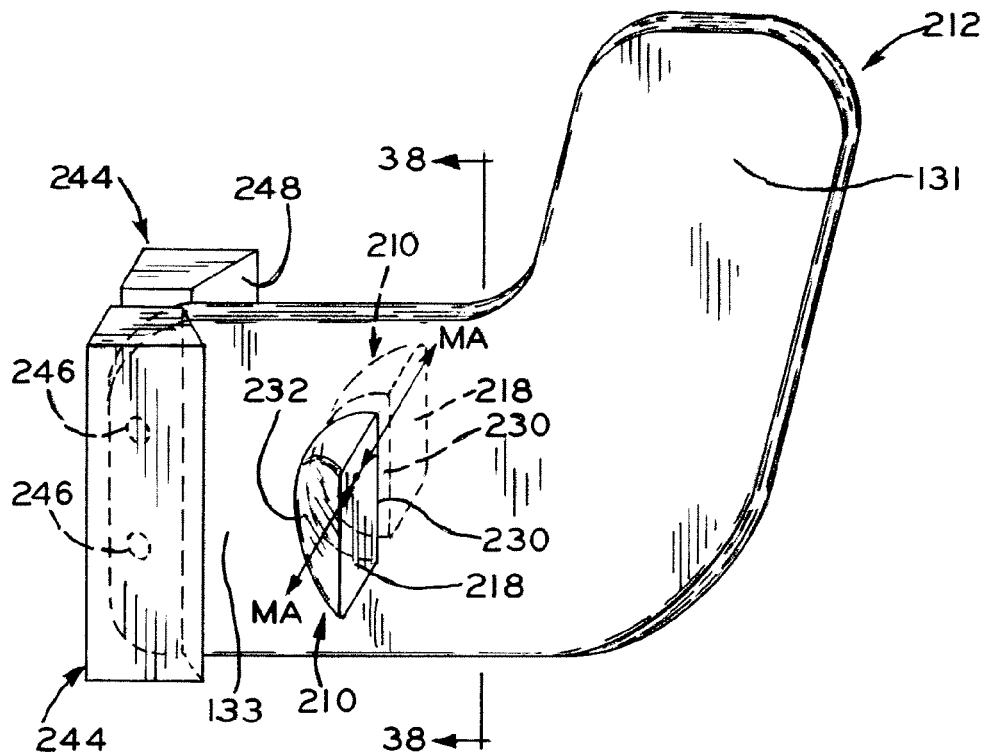
FIG. 36 is a perspective view showing a pair of retainer modules magnetically coupled on opposite sides of a delivery member.

Referring to FIG. 36, delivery member 212 is shown, which is identical to delivery member 112 discussed above, except for the addition of pusher elements 244 thereto, which are discussed below. Identical reference numerals will be used with respect to delivery members 212 and 112 to identify identical or substantially identical features therebetween.

Figure 37:
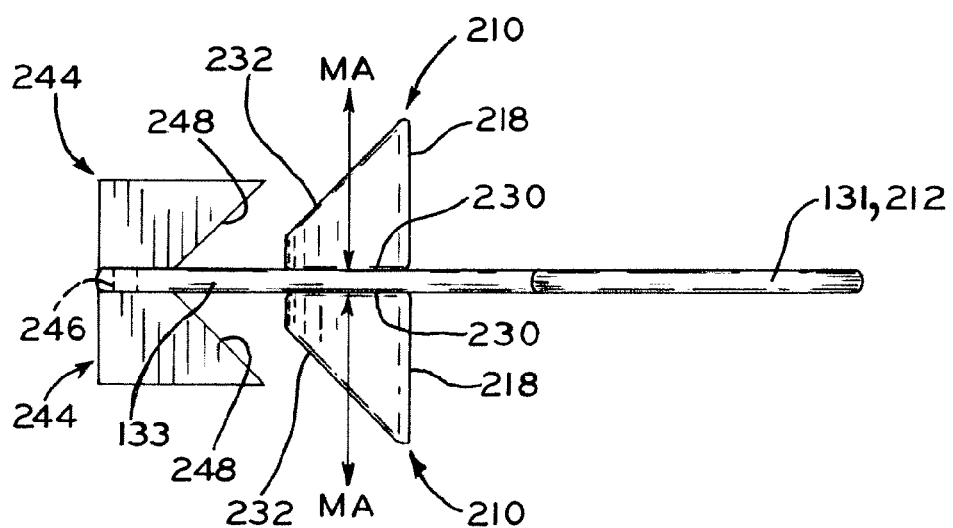
FIG. 37 is a top view of the arrangement of FIG. 36.
Figure 38:
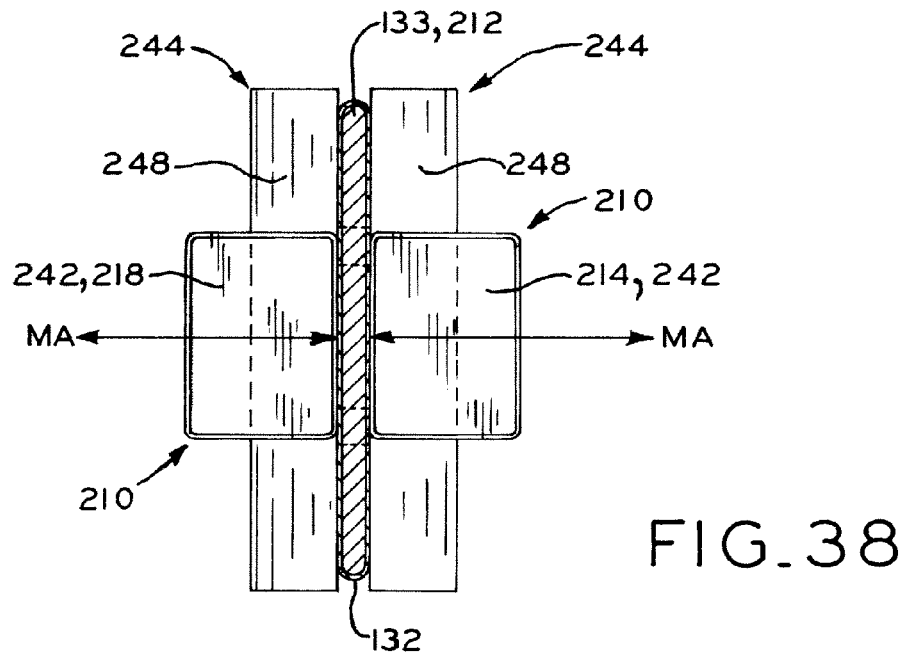
FIG. 38 is a front view of the arrangement of FIG. 36.

Referring to FIGS. 36-38, delivery member 212 in one embodiment is made of stainless steel that includes a release coating 132 of the type described above. Delivery member 212 also includes a pair of pusher elements 244 on opposite sides of the rear end of retention portion 133 thereof, which may be integrally formed with delivery member 212, or may comprise separate components attached to delivery member 212, such that pusher elements 244 are fixedly attached to delivery member 212. In one embodiment, pusher elements 244 are made of a rigid plastic material that is over-molded onto the end of retention portion 133 of delivery member 212 with the material of pusher elements 244 bridging through apertures 246 in delivery member 212 to provide a secure connection between pusher elements 244 and delivery member 212.

Pusher elements 244 each generally include a contact face 248 that is shaped to abuttingly contact or engage a retainer module 210 at any suitable location on retainer module such as, for example, lingual surface 232 of a retainer module 210, for the purpose described below. In the embodiment shown herein, contact faces 248 of pusher elements 244 are sloped or angled complementary to planar lingual surfaces 232 of retainer modules 210.

The application of a pair of retainer modules 210 to a pair of respective adjacent teeth $T_1$ and $T_2$ will now be described with reference to FIGS. 36-43B. Teeth $T_1$ and $T_2$ may be any pair of adjacent teeth in either the mandibular or the maxillar arch, and may be any type of teeth such as incisors, premolars, or molars, or adjacent teeth of different types.

Referring to FIGS. 36-38, a pair of retainer modules 210 are fitted, or magnetically coupled, to opposite sides of retention portion 133 of delivery member 212 with the interproximal surfaces 230 of modules 210 directly engaging opposite sides of retention portion 133, such that delivery member 212 is captured between modules 210. As discussed above, the mutual attraction of magnets 214 along their aligned magnetic axes MA-MA also tends to automatically rotationally and positionally align retainer modules 210 with respect to one another such that their bonding surfaces 218 are disposed parallel and co-planar to one another. In this position, rotation of one module 210 will tend to cause a corresponding rotation of the other module 210. Also, sliding movement of one module 210 along delivery member 212 will tend to cause a corresponding sliding movement of the other module 210. Modules 210 are rotated such that bonding surfaces 218 generally face toward the front end of delivery member 212, i.e., away from pusher elements 244.

Although retainer modules 210 are magnetically coupled on opposites sides of retention portion 133 of delivery member 212, retainer modules 210 are still movable or slidable relative to delivery member 212 as discussed below. After retainer modules 210 are initially coupled to delivery member 212, modules 210 may be positioned in abutment with contact faces 248 of pusher elements 244 or alternatively as shown in FIG. 37, may be spaced slightly away from contact faces 248 with a slight gap therebetween.

Advantageously, because retainer modules 210 are each slidable or movable relative to delivery member 212, the positions of retainer modules 210 with respect to delivery member 212 and/or to each other may change when bonding surfaces 218 of retainer modules 210 contact the lingual sides of a pair of respective teeth, depending on the shape of the teeth, in order to allow the positions of the retainer modules 210 to adapt to properly fit to the teeth. In this manner, the initial relative positions of retainer modules 210 on delivery member 212 will automatically be set when same are magnetically coupled to opposite sides of delivery member 212 by the alignment of the magnetic axes MA-MA of the modules 210. However, because each module 210 is independently movable relative to delivery member 212, the relative positions of modules 210 with respect to each other may vary as needed when modules 210 are mounted to their respective teeth in order to properly fit modules 210 to their respective teeth.

Referring to FIGS. 39-42, modules 210 are applied to lingual sides LS of a pair of adjacent teeth $T_1$ and $T_2$ for retaining the positions of the teeth with respect to one another in a similar manner as described above with respect to FIGS. 25-28, except for the differences described below. As described below, teeth $T_1$ and $T_2$ are in the mandibular arch, however, it will be understood that an analogous procedure may be followed if teeth $T_1$ and $T_2$ are in the maxillar arch. Also, it should be appreciated that teeth $T_1$ and $T_2$ are shown schematically in FIGS. 39-41 for clarity.

Figure 39:
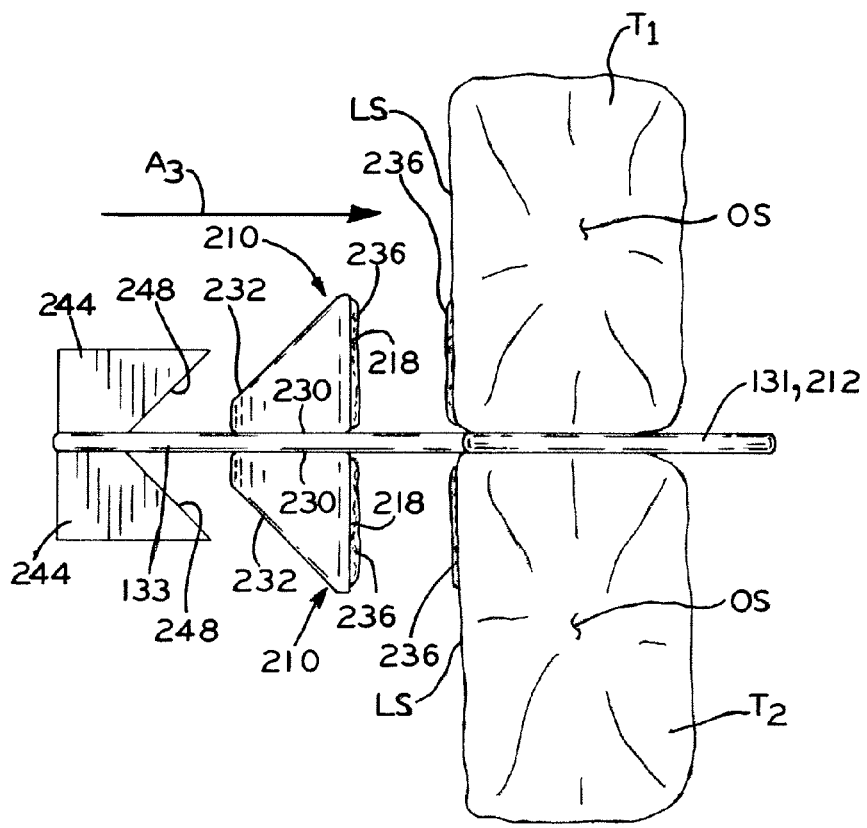
FIG. 39 is a top view showing the delivery member inserted between a pair of adjacent teeth, further showing movement of the delivery member and retainer modules along a generally lingual-facial direction.

Referring to FIG. 39, the lingual sides LS of teeth $T_1$ and $T_2$ may be prepared for receipt of an amount of adhesive 236 in a conventional manner, in which the lingual sides of teeth $T_1$ and $T_2$ are dried and acid etched, for example. An amount of a primer (not shown) may be applied to the etched teeth for receipt of a small amount of adhesive 236 to the primer.

Prior to insertion of delivery member 212 and retainer modules 210 into the oral cavity, an amount of adhesive 236 may also be applied to bonding surfaces 218 of modules 210 which, as described above, may already include a layer or cap 242 of cured adhesive, or may be directly exposed. Advantageously, when bonding surfaces 218 of modules 210 includes a cap or layer 242 of adhesive 236 that has been cured, application of an additional amount of adhesive 236 thereto, followed by subsequent curing of the adhesive to both the previously cured adhesive of cap or layer 242 and also to amount of adhesive on the lingual sides LS of teeth $T_1$ and $T_2$ forms an adhesive/adhesive/adhesive bond that is particularly robust in retaining modules 210 in place on the lingual sides of teeth $T_1$ and $T_2$.

Figure 42:
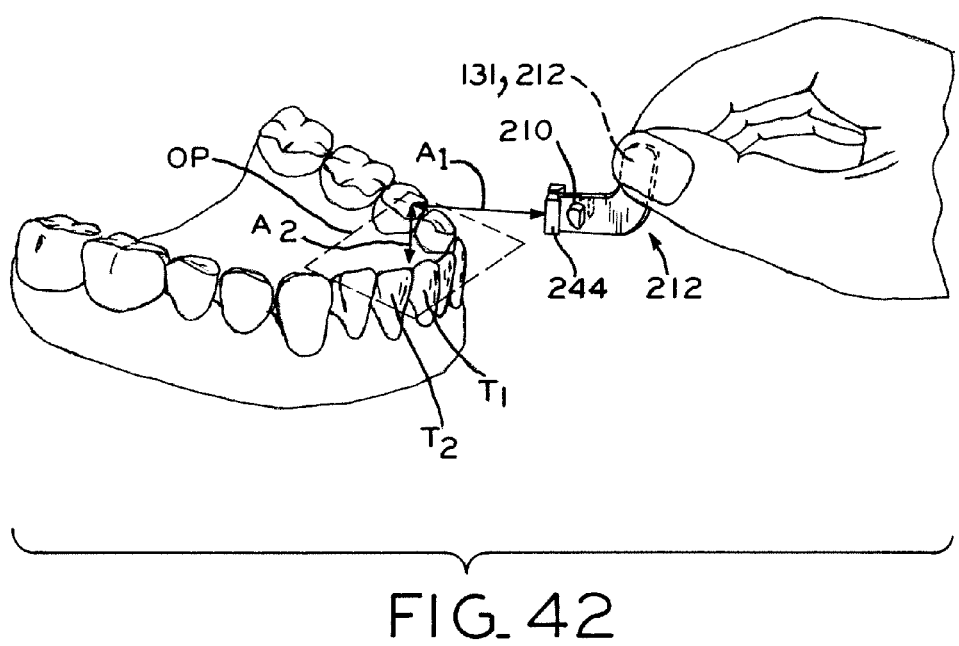
FIG. 42 is a perspective view of a portion of a patient's mouth, depicting the initial insertion of the delivery member and retainer modules between a pair of the patient's teeth, and withdrawal of the delivery member after the retainer modules have been placed.

Referring to FIGS. 39 and 42, delivery member 212 is inserted between the pair of adjacent teeth $T_1$ and $T_2$ by the orthodontist gripping the gripping portion 131 of delivery member 212 and inserting delivery member 212 into the oral cavity of the patient along the general direction of arrow $A_1$ in FIG. 42, which is substantially parallel to the occlusal plane defined by the occlusal surfaces OS of the teeth in the arch. Once positioned within the oral cavity of the patient, delivery member is inserted between teeth $T_1$ and $T_2$ along a generally downward direction (upward if $T_1$ and $T_2$ are maxillar) along the general direction of arrow $A_2$ in FIG. 42 from the occlusal surfaces OS of teeth $T_1$ and $T_2$, and through the occlusal plane OP defined by occlusal surfaces OS toward the gum tissue. The foregoing directions depicted by arrows $A_1$ and $A_2$ in FIG. 42 may comprise a single, continuous motion.

Advantageously, as may be seen from FIG. 42, the shape of delivery member 112, 212 allows gripping portion 131 of delivery member, and thus the orthodontist's fingers, to remain substantially on a side of the occlusal plane OP of teeth $T_1$ and $T_2$ that is opposite the gum tissue around teeth $T_1$ and $T_2$ throughout the procedure, such that the orthodontist does not need to significantly move, manipulate, or depress the patient's lips or cheeks to provide access for placing the delivery member 212.

In this position, as shown in FIG. 39, a small gap will be present between the tooth-facing surfaces 218 of retainer modules 210 and the lingual sides LS of teeth $T_1$ and $T_2$.

As described below, pusher elements 244 are not connected to modules 210, but rather only abuttingly contact modules 210 for the temporary application of a force to modules 210 through movement of delivery member 212 in order to press modules 210 against the lingual sides of their respective teeth to facilitate a robust adhesive bond.

Delivery member 212 is then advanced in a lingual-facial direction along the arrow $A_3$ in FIG. 39, which direction is generally parallel to the occlusal plane OP (FIG. 28) defined by the occlusal surfaces of teeth $T_1$ and $T_2$.

Figure 40:
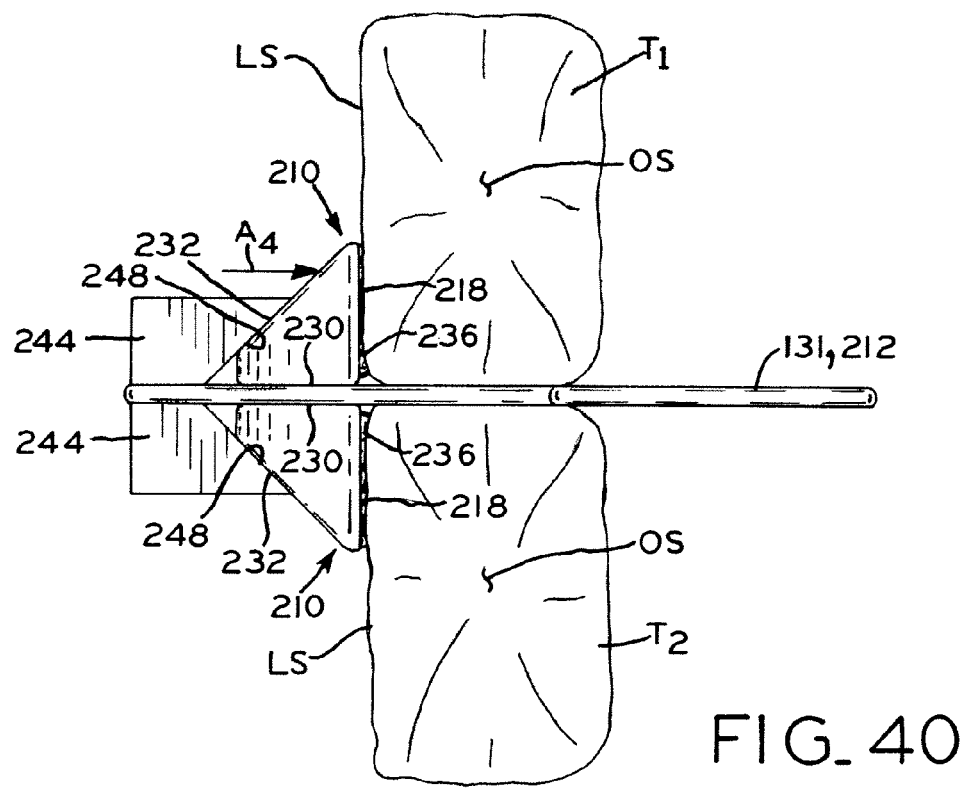
FIG. 40 is another top view showing the capture of the retainer modules between the pusher elements of the delivery member and the lingual sides of the teeth.

As may be seen between FIGS. 39 and 40, if modules 210 have been previously positioned in contact with pusher elements 244, delivery member 212, pusher elements 244, and modules 210 will all move together as a unit when delivery member 212 is advanced as described above to in turn advance modules 210 into respective engagement with the lingual sides LS of teeth $T_1$ and $T_2$.

Alternatively, if modules 210 are initially spaced slightly away from pusher elements 244, delivery member 212, pusher elements 244, and modules 210 will all move together when delivery member 212 is advanced as described above, until modules 210 engage the lingual sides LS of teeth $T_1$ and $T_2$. Then, upon further advancement of delivery member 212, modules 210 will remain stationary against the lingual sides LS of teeth $T_1$ and $T_2$, with delivery member 212 and pusher elements 244 moving relative to modules 210 until pusher elements 244 engage modules 210.

After either of the foregoing movements, modules 210 will be captured between pusher elements 244 and the lingual sides LS of teeth $T_1$ and $T_2$ as shown in FIG. 40. Thereafter, the orthodontist may exert a force by pulling on delivery member 212 in the same lingual-facial direction along arrow $A_4$ in FIG. 40 to in turn apply of a slight amount of pressure to modules 210 via pusher elements 244 that will tend to force bonding surfaces 218 of modules 210 into tight engagement with the lingual sides of teeth $T_1$ and $T_2$ prior to, and during, the subsequent curing of adhesive 236 to thereby enhance the quality of the adhesive bond between modules 210 and teeth $T_1$ and $T_2$.

As shown in FIG. 40, pusher elements 244 may be dimensioned such that bonding surfaces 218 of modules 210 extend outwardly from delivery member 212 a greater distance than pusher elements 244, which tends to maximize the exposure of bonding surfaces 218 of modules 210 to their respective teeth $T_1$ and $T_2$, and also tends to prevent adhesive 236 from flowing over the ends of modules 210 and contacting pusher elements 244.

Figure 41:
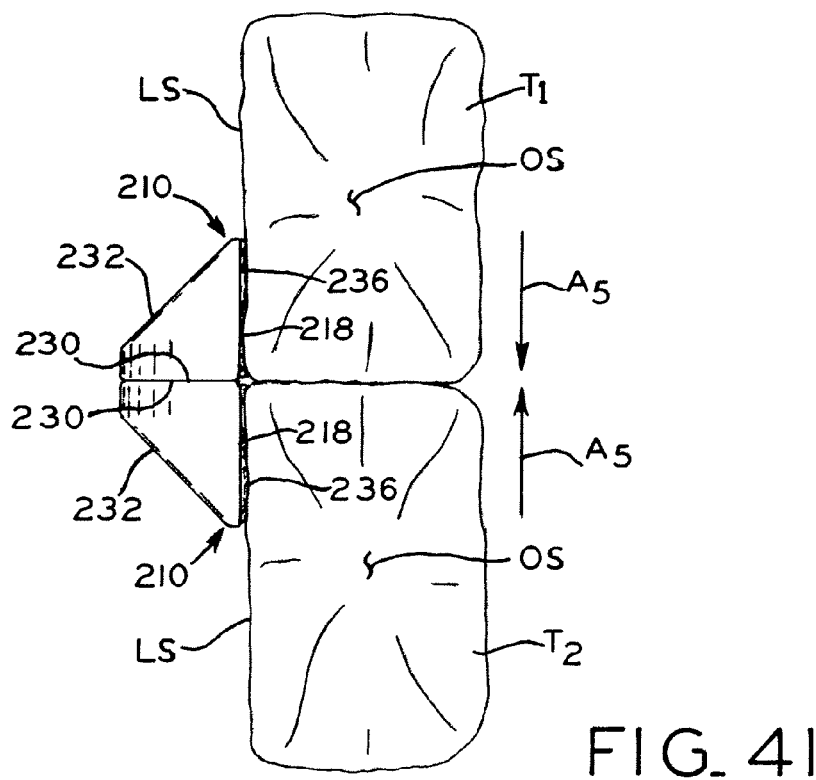
FIG. 41 is another top view of the retainer modules secured to their adjacent teeth, with the mutually-facing interproximal surfaces of the retainer modules magnetically engaging one another to aid in retaining the relative positions of the teeth.

Referring to FIGS. 41 and 42, after the adhesive 236 is cured, delivery member 212 is removed by lifting same in a generally upward direction (downward if teeth $T_1$ and $T_2$ are maxillar) in a direction generally along arrow $A_2$ in FIG. 42 opposite the insertion direction described above, i.e., in a direction from the gum surface toward the occlusal surfaces of $T_1$ and $T_2$ and through occlusal plane OP. Prior to this, delivery member 212 may be moved slightly lingually to release pusher elements 244 from contact with modules 210. Then, delivery member 212 is removed from the oral cavity of the patient along the general direction of arrow $A_1$ in FIG. 42.

After removal of delivery member 212, the teeth $T_1$ and $T_2$ may move toward one another and the planar interproximal surfaces 230 of modules 210 will typically directly engage one another by their mutual magnetic attraction, as shown by arrows $A_5$ in FIG. 41, to thereby aid in retaining teeth $T_1$ and $T_2$ in their positions adjacent one another. In particular, migration of teeth $T_1$ and $T_2$ away from one another is resisted by the magnetic attraction between modules 210, and relative lingual/facial movement of teeth $T_1$ and $T_2$ is also resisted by the magnetic engagement of modules 210 along their aligned magnetic axes MA-MA. Further, twisting or rotational movement of one tooth relative to the other is also resisted by the mutual engagement of planar interproximal surfaces 230 of modules 210.

Figure 43A:
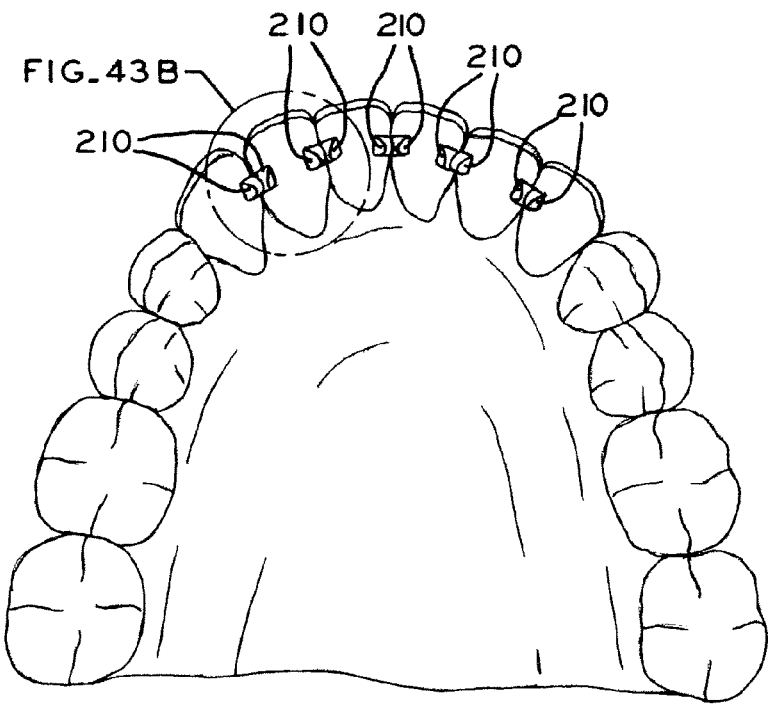
FIG. 43A is a perspective view of a dental arch, showing a series of retainer modules placed on the first incisors, second incisors, and cuspids.
Figure 43B:
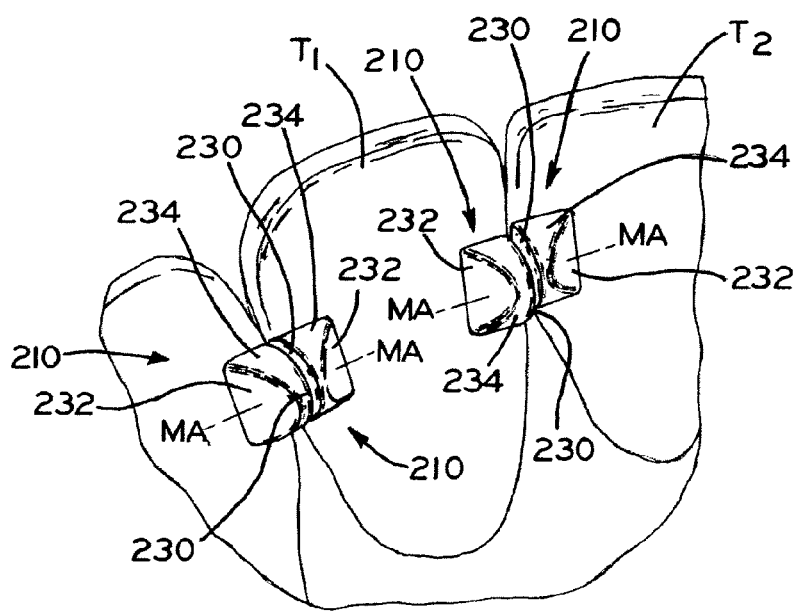
FIG. 43B is a fragmentary view of a portion of FIG. 43A.

The foregoing procedure may be repeated in a manner in which modules 210 are applied to retain a series of teeth in the dental arch, with the series of teeth mutually retained in their positions by the sets of modules 210. For example, as shown in FIGS. 43A and 43B, five sets of cooperating retainer modules 210 have been placed on the lingual sides of the first and second incisors and cuspids of a dental arch to retain these teeth in position. Advantageously, because modules 210 are freely coupled to delivery member 212, with independent movement of modules 210 with respect to delivery member 212 allowed during placement of modules as described above, modules 210 will seek their optimal positions on the teeth when secured to their respective teeth based on the shape of the lingual surfaces of the teeth. In this manner, as shown with the pair of modules to the right in FIG. 43B, the magnetic axes MA of a pair of modules 210 of a cooperating set need not be precisely aligned with one another for the interproximal surfaces 230 of the modules 210 to engage one another for retention of the teeth.

Although the magnetic attraction between the magnets 214 of a pair of adjacent modules 210 is sufficient to provide a light, constant attractive force for retaining the adjacent teeth in their desired positions, such force is generally sufficiently weak such that a patient may still apply dental floss between the teeth and the modules 210 for proper hygiene. In some cases, the dental floss may initially separate the teeth from one another when inserted between the teeth, also causing a slight separation between the modules 210 of the teeth to allow the dental floss to pass between modules 210. In other cases, the dental floss may initially directly contact the modules 210 to force same slightly apart from one another to allow the dental floss to pass therebetween. In either case, upon withdrawal of the dental floss, the contact surfaces 230 of the modules 210 will immediately re-engage with one another as described above to retain the adjacent teeth.

While this disclosure has been described as having exemplary designs, the present disclosure may be further modified within the spirit and scope of this disclosure. This application is therefore intended to cover any variations, uses, or adaptations of the disclosure using its general principles.

What is claimed is:

1. An orthodontic retainer system for use on teeth, comprising:

a pair of retainer modules, said retainer modules separate from each other and movable with respect to one another, each said retainer module comprising:
  a cover member made of a biocompatible material and including an interproximal surface;
  a rare earth magnet disposed within said cover member and defining a substantially trapezoidal shape, said rare earth magnet comprising:
    a first interproximal surface, said first interproximal surface being substantially planar and having a generally semicircular shape;
    a second surface extending substantially perpendicularly from said first surface;
    a third surface extending between said first and second surfaces to form an acute angle with respect to each of said first and second surfaces; and
    a curved fourth surface extending between said first surface and said third surface, said curved fourth surface being curved around the entirety of the generally semicircular shape of said first interproximal surface,
  said first, second, third and fourth surfaces cooperating to define the substantially trapezoidal shape as viewed in a cross-section taken in a plane perpendicular to said first and second surfaces;
  wherein said system further comprises a delivery member including a strip of material disposed between said retainer modules, said retainer modules coupled to said strip by mutual magnetic attraction of said magnets.

2. The retainer system of claim 1, wherein each retainer module further comprises a layer of adhesive disposed between each said rare earth magnet and its respective cover member, said layer of adhesive securing said magnet within said cover member.

3. The retainer system of claim 1, wherein each said cover member is made of stainless steel.

4. The retainer system of claim 1, wherein the second surface of the magnet of each said retainer module includes a tooth-facing bonding surface; wherein each said retainer module further includes a magnetic axis, said magnetic axes of said retainer modules substantially aligned, said magnetic axes rotationally positioning said retainer modules with respect to each other such that said tooth-facing bonding surfaces of said retainer modules are disposed substantially parallel to one another.

5. The retainer system of claim 4, wherein said magnetic axes of said retainer modules are parallel to said tooth-facing bonding surfaces.

6. The retainer system of claim 1, wherein each said second surface is a surface of said magnet that is not covered by said cover member.

7. The retainer system of claim 1, wherein each said second surface comprises a cap of adhesive covering a surface of said magnet that is not covered by said cover member.

8. The retainer system of claim 7, wherein each said cover member includes an open end with a rim defining a recess adjacent said second surface, said cap of adhesive disposed within said recess.

9. The retainer system of claim 1, wherein said interproximal surfaces of said cover members are in direct engagement with respective opposite sides of said strip.

10. The retainer system of claim 1, wherein said delivery member comprises:
  a gripping portion extending along a gripping portion axis; and a retention portion extending along a retention portion axis, said gripping portion joined to said retention portion at an angle such that said delivery member is substantially L-shaped.

11. The retainer system of claim 1, wherein said delivery member includes a pair of pusher elements, said pusher elements respectively engageable with said retainer modules.

12. The retainer system of claim 1, wherein said magnets have a mutual attraction force of between 0.008 lbs and 0.108 lbs depending on a distance between said magnets.

13. The orthodontic retainer system of claim 1, wherein for each of said retainer modules, said cover member has a profile that is substantially the same as said magnet.

14. The orthodontic retainer system of claim 1, wherein for each of said retainer modules said fourth surface comprises a curved surface opposite said second surface.

15. An orthodontic retainer system for use on teeth, comprising:
  a pair of retainer modules, said retainer modules separate from each other and movable with respect to one another, each said retainer module comprising:
    a magnet defining a substantially trapezoidal shape, said magnet comprising:
      a first interproximal surface, said first interproximal surface being substantially planar and having a generally semicircular shape;
      a second surface extending substantially perpendicularly from said first surface;
      a third surface extending between said first and second surfaces to form an acute angle with respect to each of said first and second surfaces; and
      a curved fourth surface extending between said first surface and said third surface, said curved fourth surface being curved around the entirety of the generally semicircular shape of said first interproximal surface, said first, second, third and fourth surfaces cooperating to define the substantially trapezoidal shape as viewed in a cross-section taken in a plane perpendicular to said first and second surfaces; and
    each said retainer module further comprises a cover member having substantially the same profile as said magnet, such that respective walls of said cover member cover respective surfaces of said magnet without substantially altering the overall shape and profile of the retainer module when said magnet is disposed within said cover member, said cover member made of a biocompatible material and including an interproximal surface; and
  wherein said system further comprises a delivery member including a strip of material disposed between said retainer modules, said retainer modules coupled to said strip by mutual magnetic attraction of said magnets, wherein the second surface of the magnet of each said retainer module includes a tooth-facing bonding surface; wherein each said retainer module comprises a magnetic axis, said magnetic axes of said retainer modules substantially aligned, said alignment of said magnetic axes urging said retainer modules into respective rotational positions with respect to each other in which said tooth-facing bonding surfaces of said retainer modules are disposed substantially parallel to one another.

16. The retainer system of claim 15, wherein said magnetic axes of said retainer modules are parallel to said tooth-facing bonding surfaces.

17. The retainer system of claim 15, wherein each said tooth-facing bonding surface is a surface of said magnet that is not covered by said cover member.

18. The retainer system of claim 15, wherein each said tooth-facing bonding surface comprises a cap of adhesive covering a surface of said magnet that is not covered by said cover member.

19. The retainer system of claim 18, wherein each said cover member includes an open end with a rim defining a recess adjacent said bonding surface, said cap of adhesive disposed within said recess.

20. The retainer system of claim 15, wherein said delivery member comprises:
  a gripping portion extending along a gripping portion axis; and
  a retention portion extending along a retention portion axis, said gripping portion joined to said retention portion at an angle such that said delivery member is substantially L-shaped.

21. The retainer system of claim 15, wherein said delivery member includes a pair of pusher elements, said pusher elements respectively engageable with said retainer modules.

22. The retainer system of claim 15, wherein said interproximal surfaces of said cover members are in direct engagement with respective opposite sides of said strip.

23. The retainer system of claim 15, wherein each retainer module further comprises a layer of adhesive disposed between each said magnet and its respective cover member, said layer of adhesive securing said magnet within said cover member.

24. The retainer system of claim 15, wherein each said cover member is made of stainless steel.

* * * * *